US010143804B2

(12) United States Patent
Gertz et al.

(10) Patent No.: US 10,143,804 B2
(45) Date of Patent: Dec. 4, 2018

(54) BIOPOLYMER-BASED EMULSION LUBRICANTS FOR SYRINGE BARRELS

(71) Applicant: ZebraSci, Inc, Temecula, CA (US)

(72) Inventors: Frederick Talley Gertz, Riverside, CA (US); Jaan Noolandi, La Jolla, CA (US); Robert James Schultheis, Temecula, CA (US)

(73) Assignee: ZebraSci, Inc, Temecula, CA (US)

( * ) Notice: Subject to any disclaimer, the term of this patent is extended or adjusted under 35 U.S.C. 154(b) by 374 days.

(21) Appl. No.: 15/164,148

(22) Filed: May 25, 2016

(65) Prior Publication Data

US 2016/0346477 A1 Dec. 1, 2016

Related U.S. Application Data

(60) Provisional application No. 62/168,102, filed on May 29, 2015.

(51) Int. Cl.

| | |
|---|---|
| ***A61M 5/31*** | (2006.01) |
| ***C10M 145/40*** | (2006.01) |
| ***C10M 173/02*** | (2006.01) |

(52) U.S. Cl.

CPC ........ *A61M 5/3129* (2013.01); *C10M 145/40* (2013.01); *C10M 173/02* (2013.01); *A61M 2005/3131* (2013.01); *C10M 2209/12* (2013.01); *C10M 2229/025* (2013.01); *C10N 2230/02* (2013.01); *C10N 2230/06* (2013.01); *C10N 2240/66* (2013.01); *C10N 2250/02* (2013.01); *C10N 2250/04* (2013.01)

(58) Field of Classification Search

CPC ........ A61M 5/3129; A61M 2005/3131; C10M 173/02; C10M 145/40; C10M 2229/025; C10M 2209/12; C10N 2230/06; C10N 2230/02; C10N 2250/02; C10N 2240/66; C10N 2250/04

See application file for complete search history.

(56) References Cited

U.S. PATENT DOCUMENTS

| | | | | |
|---|---|---|---|---|
| 5,795,591 | A | 8/1998 | Lee | |
| 6,673,753 | B2 | 1/2004 | Person Hei | |
| 2004/0231926 | A1 | 11/2004 | Sakhrani | |
| 2005/0112186 | A1 | 5/2005 | Devore | |
| 2008/0026026 | A1 | 1/2008 | Lu | |
| 2015/0126941 | A1* | 5/2015 | Felts | A61M 3/0262 604/230 |

OTHER PUBLICATIONS

Ashok R. Patel et al. (Biopolymer Based Structuring of Liquid Oil into Soft Solids and Oleogels Using Water-Continuous Emulsions as Templates), 2015, Langmuir (Year: 2015).*

(Continued)

*Primary Examiner* — Taiwo Oladapo

(74) *Attorney, Agent, or Firm* — Lumen Patent Firm

(57) ABSTRACT

A stable biopolymer-based emulsion lubricant including Agar is provided to reduce the friction between a syringe barrel plunger and the interior surface of the syringe barrel. According to exemplary embodiments the emulsion has a friction of less than 4N, the emulsion is temperature stable in a range of 4-23 degrees Celsius and the emulsion is stable for a period of at least 60 days.

16 Claims, 30 Drawing Sheets

(56) References Cited

OTHER PUBLICATIONS

Patel et al. Biopolymer-Based Structuring of Liquid Oil into Soft Solids and Oleogels Using Water-Continuous Emulsions as Templates. Langmuir, 2015, 31 (7), pp. 2065-2073.
Chan et al. Syringe Siliconization Process Investigation and Optimization. J. Pharm. Sci. and Tech. 2012, 66 136-150.
Cilurzo et al. Injectability Evaluation: An Open Issue, AAPS PharmSciTech, vol. 12, No. 2, Jun. 2011, pp. 604-609.

* cited by examiner

| Figure # | Description of Weight Compositions | Oil Mass (g) | Mass of Polysaccharide (g) | Polysaccharide solvent mass (g) | Gelling agent mass (g) | Gelling agent solvent mass (g) |
|---|---|---|---|---|---|---|
| Figure 6 | 2 wt. % Xanthan Gum - 6 wt. % Agar (80:20) | 160 | 0.6 | 29.4 | 0.6 | 9.4 |
| Figure 8 | 2 wt. % Xanthan Gum - 1 wt. % Agar (60:40) | 120 | 1.2 | 58.8 | 1.2 | 18.8 |
| Figure 10 | 2 wt. % Xanthan Gum - 1 wt. % Agar (60:40) | 120 | 1.2 | 58.8 | 1.2 | 18.8 |
| Figure 12 | 1 wt. % Agar (60:40) | 120 | N/A | N/A | 0.8 | 79.2 |
| Figure 14 | 1 wt. % Agar (60:40) | 120 | N/A | N/A | 0.8 | 79.2 |
| Figure 16 | 2 wt. % Dextran - 1 wt. % Agar (60:40) | 120 | 1.2 | 58.8 | 0.2 | 19.8 |
| Figure 18 | 2 wt. % Dextran - 1 wt. % Agar (60:40) | 120 | 1.2 | 58.8 | 0.2 | 19.8 |
| Figure 20 | 2 wt. % CMC - 1 wt. % Agar (60:40) | 120 | 1.2 | 58.8 | 0.2 | 19.8 |
| Figure 22 | 1 wt. % Agar (60:40) | 120 | N/A | N/A | 0.8 | 79.2 |
| Figure 24 | 1 wt. % Agar (60:40) | 120 | N/A | N/A | 0.8 | 79.2 |
| Figure 26 | 2 wt. % Xanthan Gum - 1 wt. % Agar (60:40) | 120 | 1.2 | 58.8 | 1.2 | 18.8 |
| Figure 28 | 2 wt. % Dextran - 1 wt. % Agar (60:40) | 120 | 1.2 | 58.8 | 1.2 | 18.8 |

FIG. 30

BIOPOLYMER-BASED EMULSION LUBRICANTS FOR SYRINGE BARRELS

CROSS-REFERENCE TO RELATED APPLICATIONS

This application claims priority from U.S. Provisional Patent Application 62/168,102 filed May 29, 2015, which is incorporated herein by reference.

FIELD OF THE INVENTION

The invention relates to methods for the establishment of biopolymer-based emulsion lubricant coverage on the interior surface of syringe barrels to for example reduce friction. The invention also relates to syringe barrels with the interior surface covered with a biopolymer-based emulsion lubricant.

BACKGROUND OF THE INVENTION

Syringes already filled with an aqueous-based drug solution play an increasingly important role in the pharmaceutical industry and the medical community. Within the industry community, these pre-filled syringes represent a market share of over $2 billion dollars, with over 60 products on the market and a growing number of protein-based products expected to enter the market in the near future.

From a medical standpoint, pre-filled syringes allow for improved drug delivery that is less wasteful, safer, and frequently easy enough for patients to do without the oversight of a medical professional.

An important part of the syringe is the plunger system, which relies on a layer of lubricant to allow for an ideal glide force and ensuring complete delivery of the drug product within the specific injection time and force.

The most common lubricant is silicone-based oil, and the siliconization of these syringes, understandably has played an important part in the development of pre-filled syringes. As well as providing an ideal glide force and ensuring that the plunger travels the full path, siliconization also provides several advantages. It is a hydrophobic oil allowing for easy emptying of a drug product, and an oil that is low reacting, frequently used as a buffer layer between the syringe barrel and the drug product ensuring no reaction takes place between the two materials.

For sensitive applications, such as injections into the human eye for treatment, silicone oil droplets are observable within patients with an unknown amount of resulting damage.

As the FDA and other governing bodies work to eliminate the danger of these and other leachables, it is important to develop technology that will provide for the establishment of a stable lubricant layer on the interior of the syringe barrel.

SUMMARY OF THE INVENTION

A medical drug delivery device is provided, such as a syringe barrel, with an interior surface lubricated with an emulsion of a hydrophobic liquid oil in a matrix of water-soluble polysaccharides, where one type of the polysaccharide is Agar. In one example the emulsion contains 1-10 percent Agar. The emulsion contains a polysaccharide filler such as Xantham Gum, Dextrum, Cellulose, or a combination thereof. The hydrophobic liquid oil has a viscocity in the range 20-12,500 cSt, more specifically in the range of 20-1000 cSt. One of the objectives of the biopolymer-based emulsion lubricants of this invention is to reduce the friction between a syringe barrel plunger and the interior surface of the syringe barrel as well as to provide a stable syringe barrel lubricant. According to exemplary embodiments the emulsion has a friction of less than 4N, the emulsion is temperature stable in a range of 4-23 degrees Celsius and the emulsion is stable for a period of at least 60 days.

A method of lubricating a medical drug delivery device is also provided. The method includes spraying an emulsion as described supra onto the interior surface of a syringe barrel. In one example, the emulsion is sprayed on with a volume of 0.5-10 microliter and with a flow rate of 1-5 standard liter per minute. The spaying could start at about 30 mm outside the syringe barrel and stops at about 40 mm inside the syringe barrel for a duration of about 1 second.

BRIEF DESCRIPTION OF THE DRAWINGS

FIG. 30 shows a table with weight compositions for FIGS. 6-29 according to exemplary embodiments of the invention.

DETAILED DESCRIPTION

Preparation of Emulsions

According to exemplary embodiments as shown in the figures, for mixing hydrophobic liquid oil in a matrix of water-soluble biopolymers we used Dow Corning oil, with a viscosity of 20 centistokes (cSt). In other embodiments, we used 500 cSt and 1000 cSt with Agar (Sigma-Aldrich, St. Louis, Mo.), Xanthan Gum (Cargill, Minneapolis, Minn.), Dextran (Sigma-Aldrich, St. Louis, Mo.) and/or CarboxyMethyl Cellulose (CMC) (Modernist Pantry, Portsmouth, N.H.)

Emulsions with Agar were prepared with 60% wt of oil and 40% wt water phase. The water phase had a 3:1 ratio by wt of Xanthan Gum: Agar stock solutions. Emulsions with 80% wt of oil and 20% wt water phase were also made.

As an example for 60% wt of oil and 40% wt of water phase for the Agar based emulsion, the stock solutions were prepared as follows:

Starting with 240 gm oil, 160 gm water phase, the water phase consisted of 120 gm Xanthan Gum solution, 40 gm of Agar solution.

For 2% wt solution of Xanthan Gum, this gave 120×0.98=117.6 gm water and 120×0.02=2.4 gm Xanthan Gum.

For 6% wt solution of Agar this gave 40×0.94=37.6 gm water and 40×0.06=2.4 gm Agar.

Figure 1:
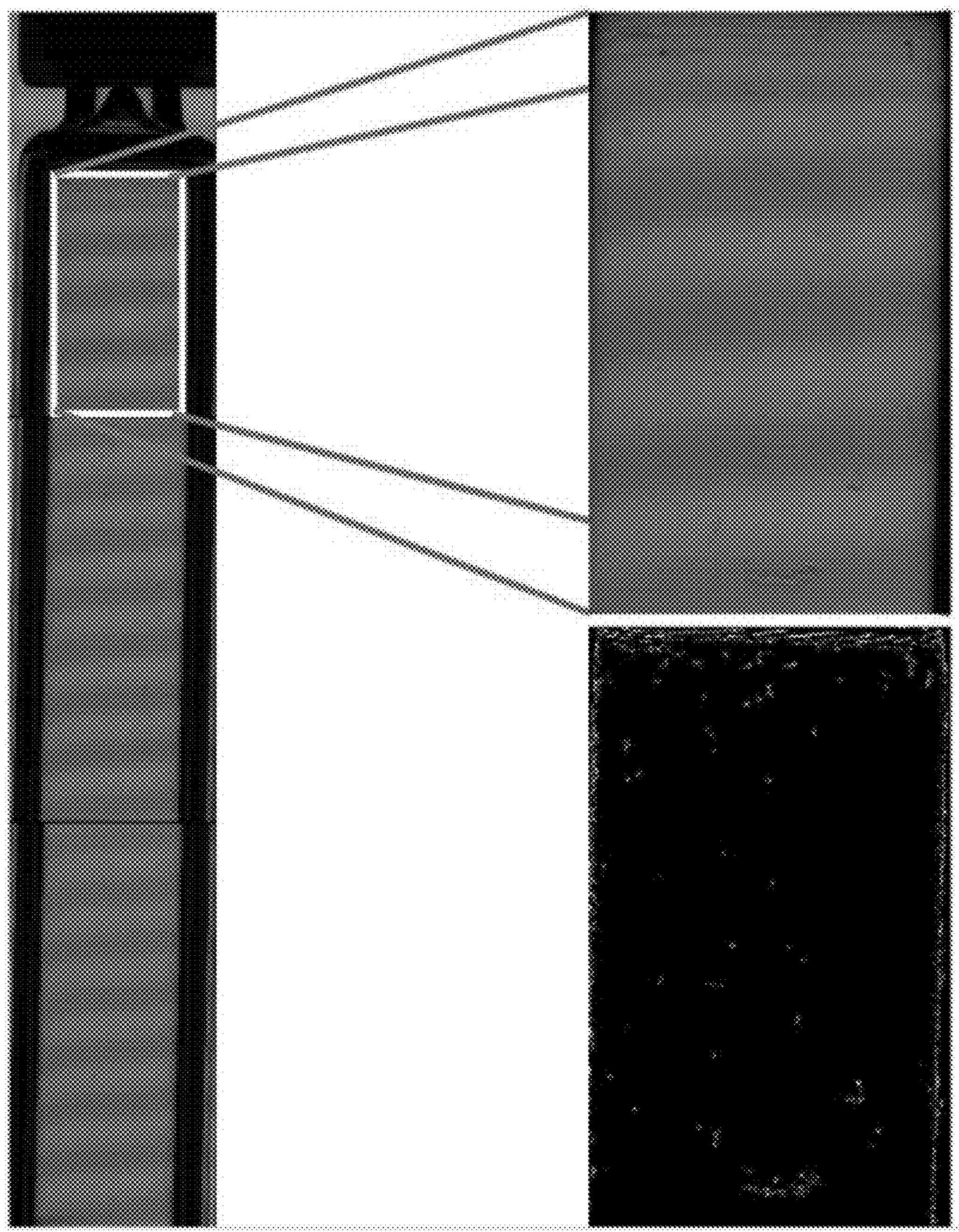
FIG. 1 shows an image of an empty glass syringe barrel before spraying with lubricant according to an exemplary embodiment of the invention. The top right image in the FIG. 1 is an expanded view of the glass syringe barrel. The bottom right image in FIG. 1 is an image with a Canny Edge detection algorithm (The Mathworks, Sunnyvale, Calif.) applied to the top right image to highlight the edge of silicone oil droplets.
Figure 2:
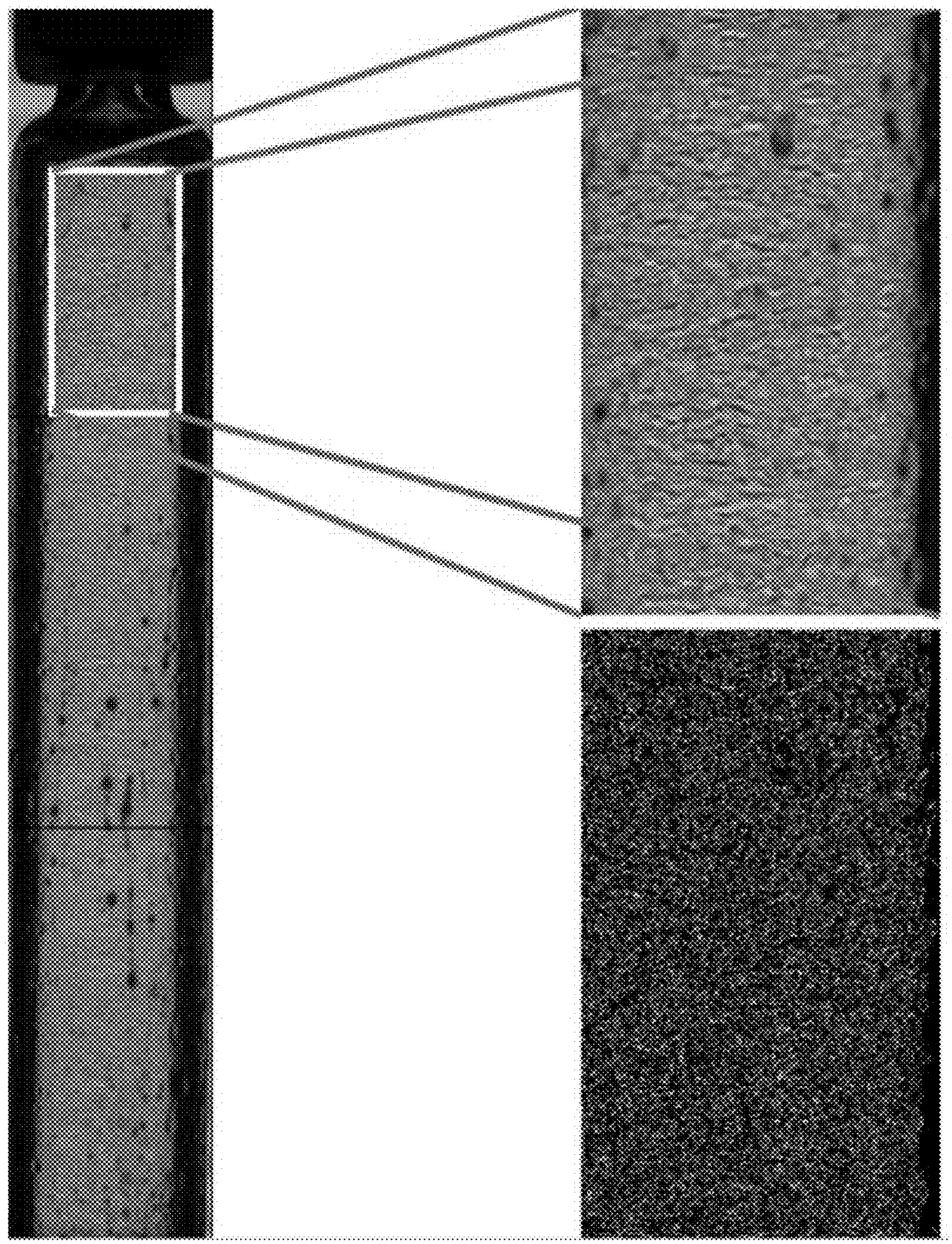
FIG. 2 shows according to an exemplary embodiment of the invention an image of a glass syringe barrel with a fresh emulsion spray of 500 cSt Silicone Oil. The spray is composed of 80% oil/20% water mixture. The water mixture has it in 2% Xantham Gum and 6% Agar by wt solution. The top right image in the FIG. 2 is an expanded view of the glass syringe barrel. The bottom right image in FIG. 2 is an image with a Canny Edge detection algorithm (The Mathworks, Sunnyvale, Calif.) applied to the top right image to highlight the edge of silicone oil droplets.
Figure 3:
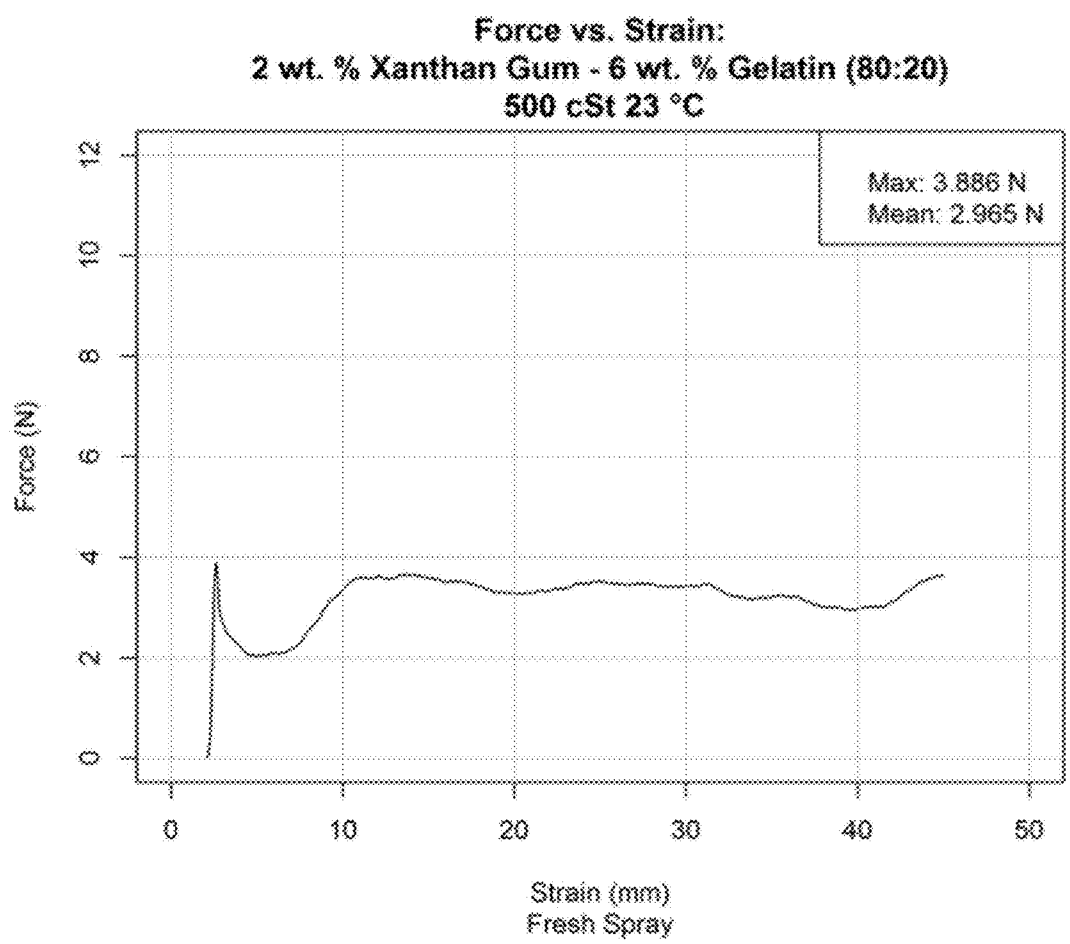
FIG. 3 shows according to an exemplary embodiment of the invention glide force measurements for FIG. 2.
Figure 4:
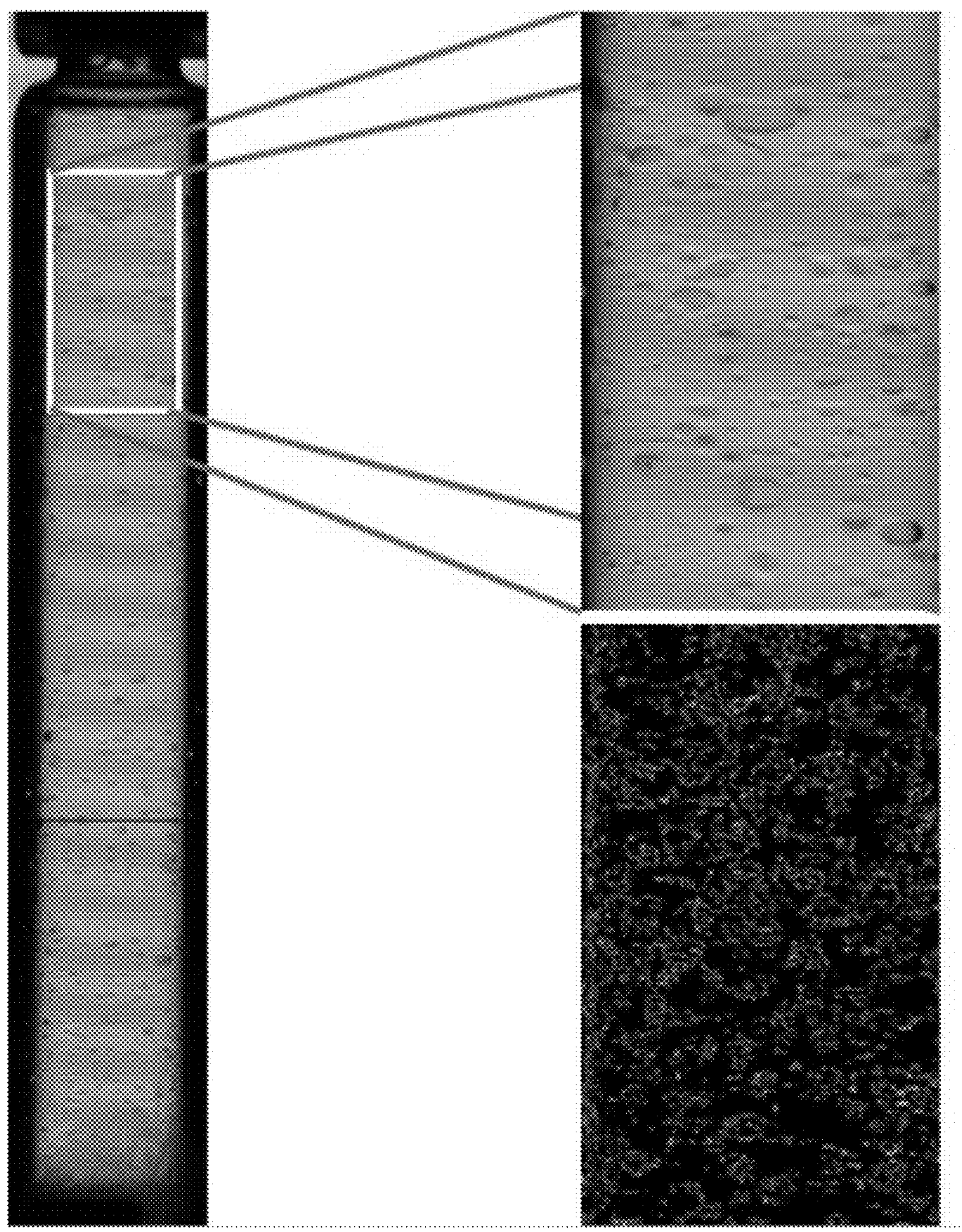
FIG. 4 shows according to an exemplary embodiment of the invention an image of a glass syringe barrel with an emulsion spray of 500 cSt Silicone Oil. The spray is composed of 80% oil/20% water mixture. The water mixture has in it 2% Xantham Gum and 6% Agar by wt solution. The glass syringe barrel has been filled with an aqueous-based solution and kept for 27 days at 40° C. The top right image in the FIG. 4 is an expanded view of the glass syringe barrel. The bottom right image in FIG. 4 is an image with a Canny Edge detection algorithm (The Mathworks, Sunnyvale, Calif.) applied to the top right image to highlight the edge of silicone oil droplets.
Figure 5:
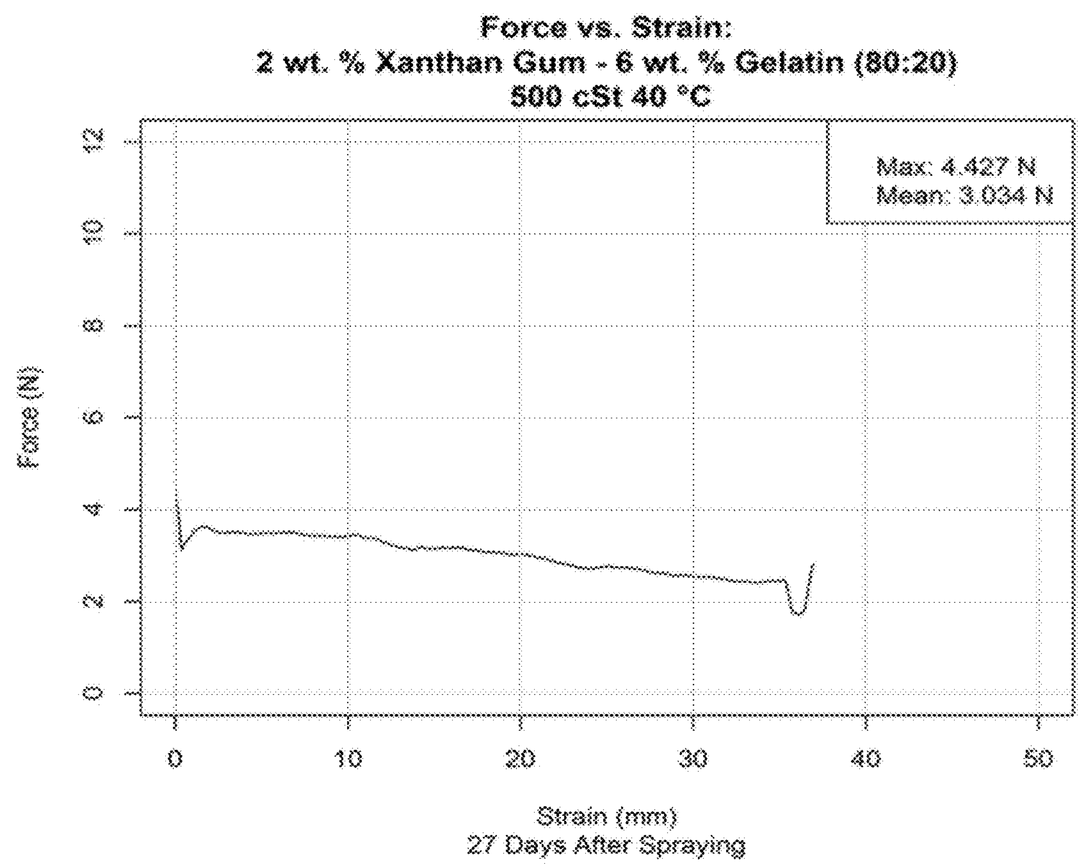
FIG. 5 shows according to an exemplary embodiment of the invention glide force measurements for FIG. 4.
Figure 6:
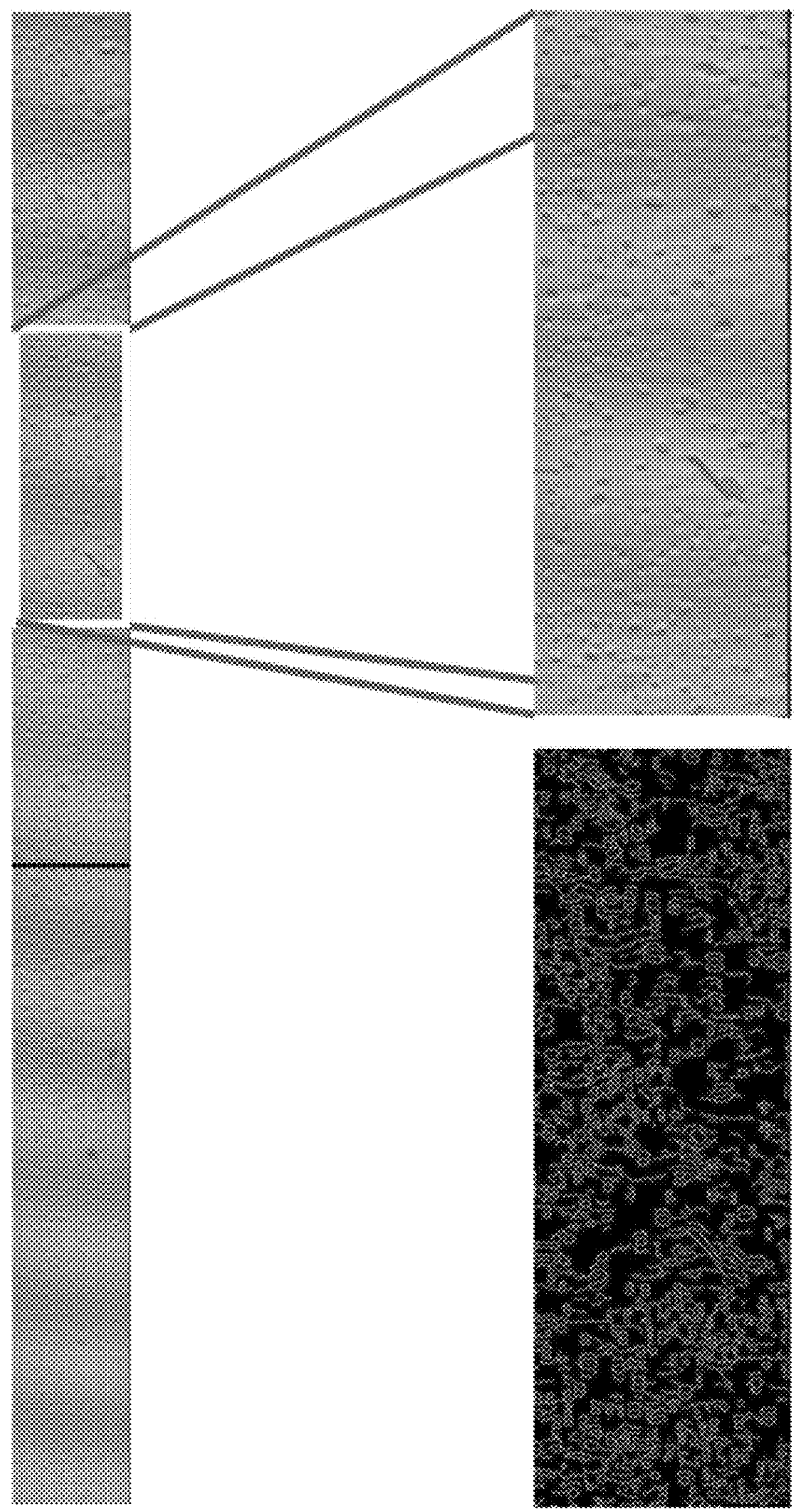
FIG. 6 shows according to an exemplary embodiment of the invention an image of a glass syringe barrel with an emulsion spray of 500 cSt Silicone Oil. The spray is composed of 80% oil/20% water mixture. The water mixture has in it 2% Xantham Gum and 6% Agar by wt solution. The glass syringe barrel has been filled with an aqueous-based solution and kept for 57 days at 4° C. The top right image in the FIG. 6 is an expanded view of the glass syringe barrel. The bottom right image in FIG. 6 is an image with a Canny Edge detection algorithm (The Mathworks, Sunnyvale, Calif.) applied to the top right image to highlight the edge of silicone oil droplets.
Figure 7:
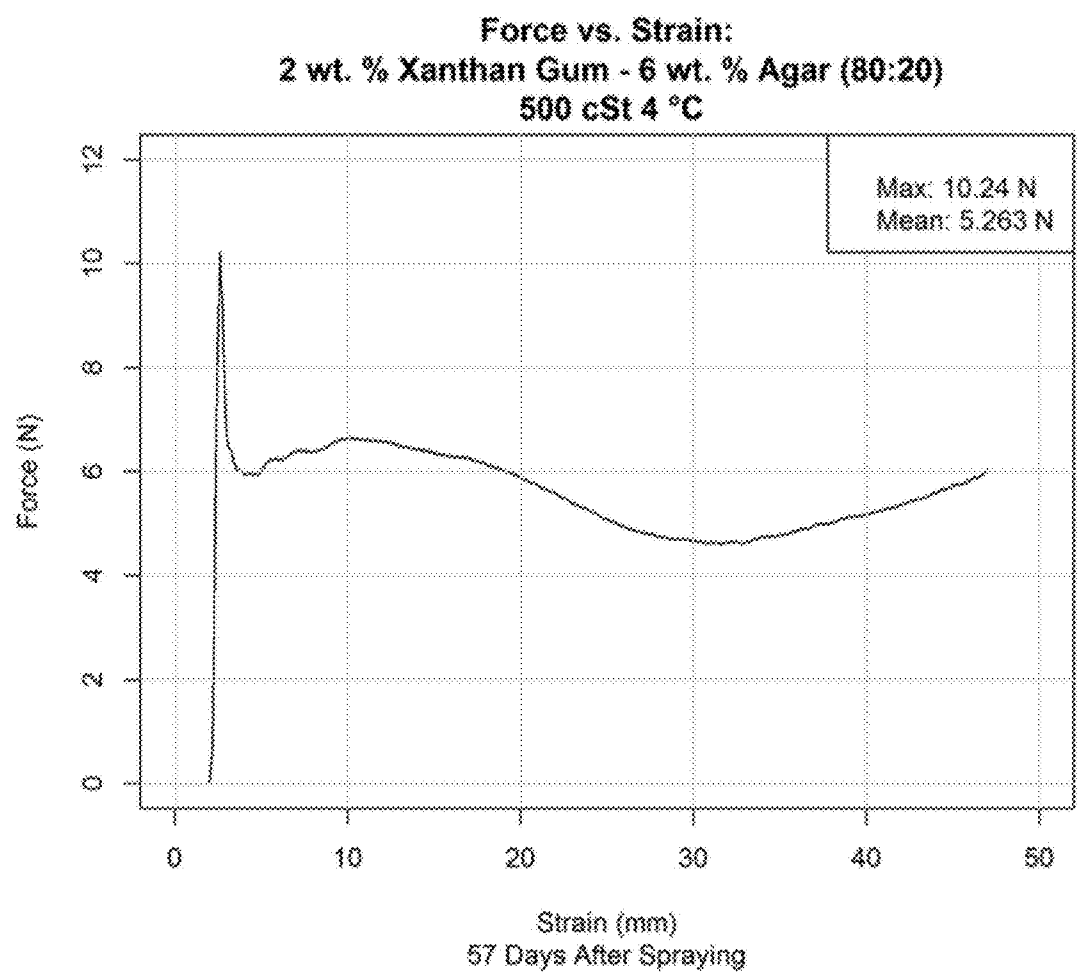
FIG. 7 shows according to an exemplary embodiment of the invention glide force measurements for FIG. 6.
Figure 8:
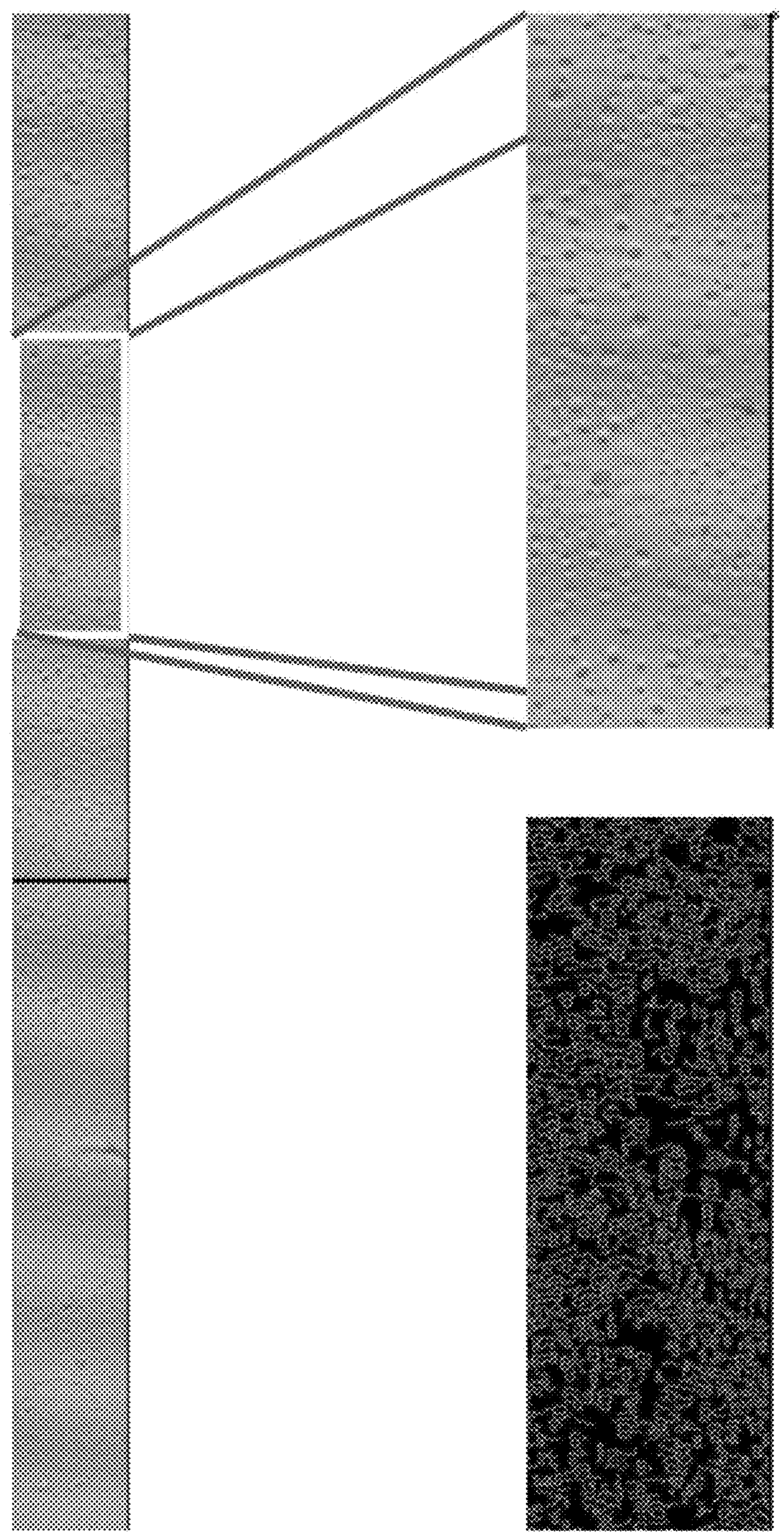
FIG. 8 shows according to an exemplary embodiment of the invention an image of a glass syringe barrel with an emulsion spray of 500 cSt Silicone Oil. The spray is composed of 60% oil/40% water mixture. The water mixture has in it 2% Xantham Gum and 1% Agar by wt solution. The glass syringe barrel has been filled with an aqueous-based solution and kept for 57 days at 23° C. The top right image in the FIG. 8 is an expanded view of the glass syringe barrel. The bottom right image in FIG. 8 is an image with a Canny Edge detection algorithm (The Mathworks, Sunnyvale, Calif.) applied to the top right image to highlight the edge of silicone oil droplets.
Figure 9:
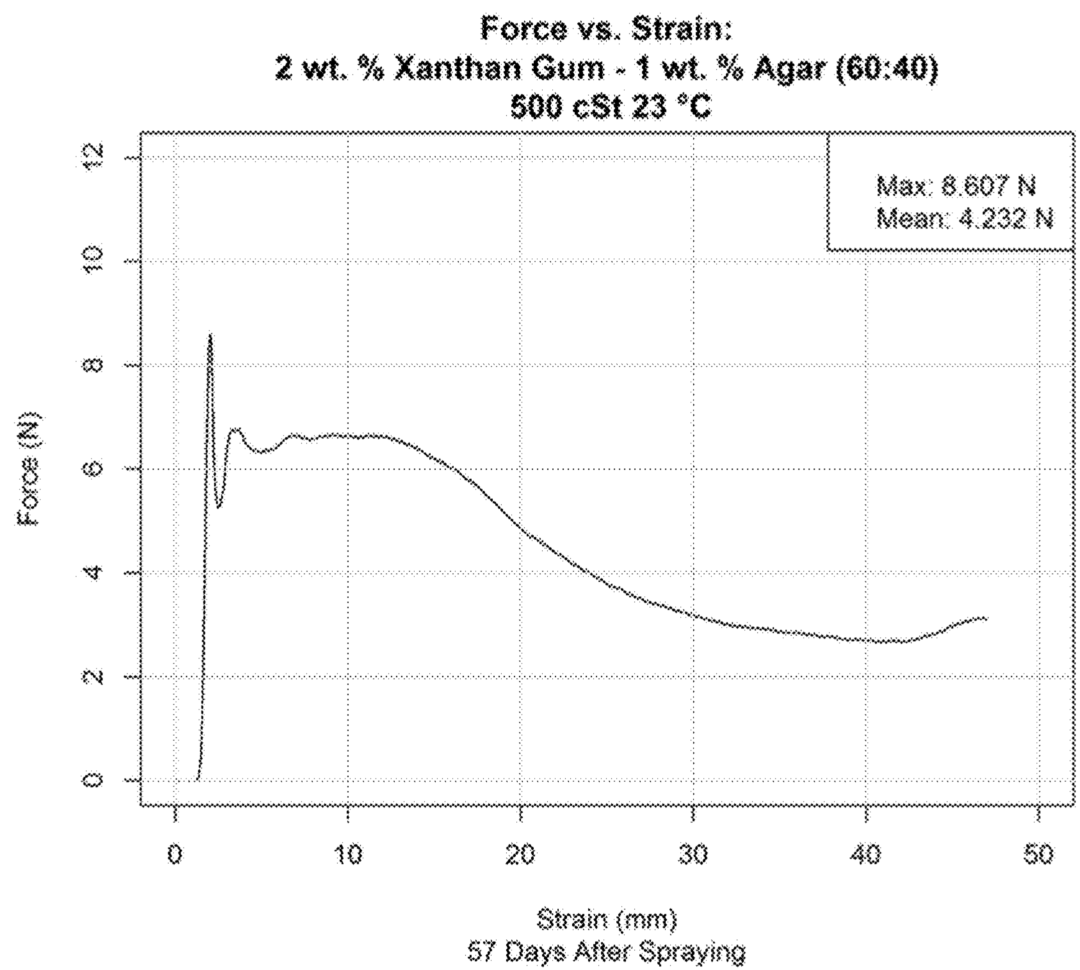
FIG. 9 shows according to an exemplary embodiment of the invention glide force measurements for FIG. 8.
Figure 10:
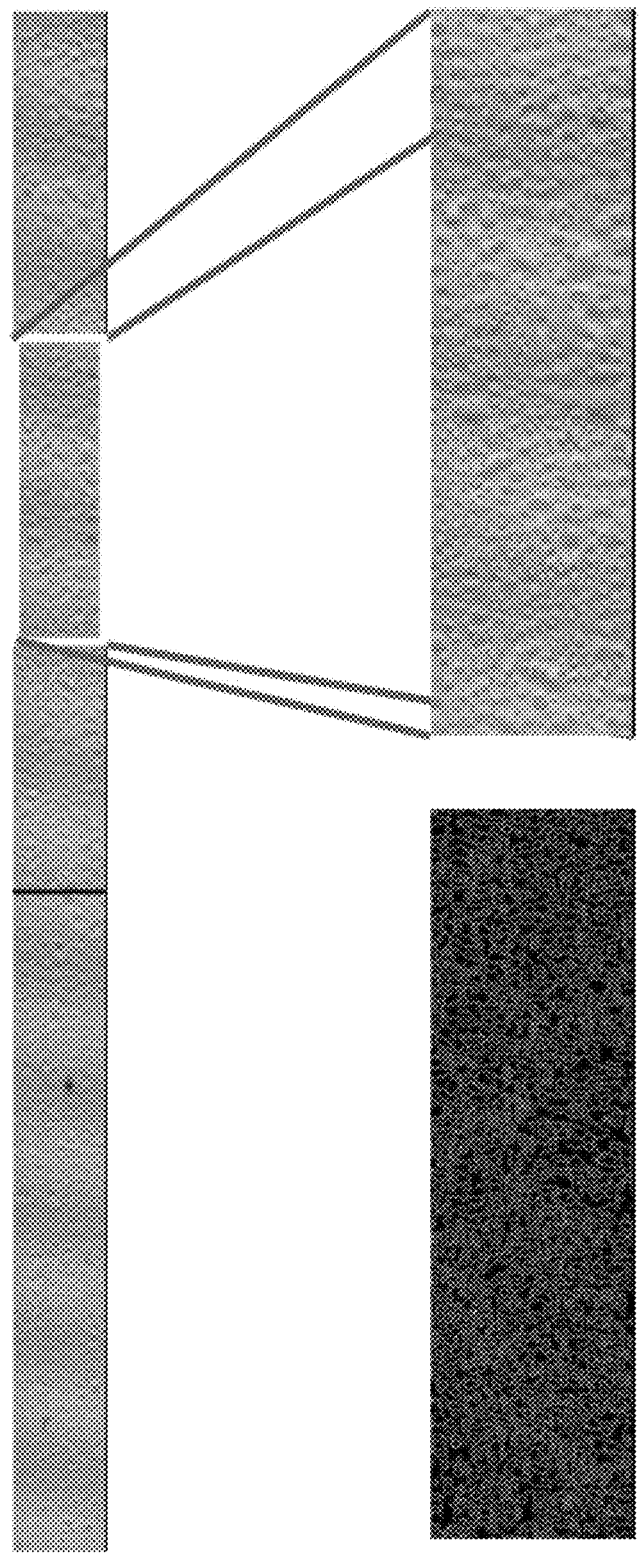
FIG. 10 shows according to an exemplary embodiment of the invention an image of a glass syringe barrel with an emulsion spray of 500 cSt Silicone Oil. The spray is composed of 60% oil/40% water mixture. The water mixture has in it 2% Xantham Gum and 1% Agar by wt solution. The glass syringe barrel has been filled with an aqueous-based solution and kept for 57 days at 4° C. The top right image in the FIG. 10 is an expanded view of the glass syringe barrel. The bottom right image in FIG. 10 is an image with a Canny Edge detection algorithm (The Mathworks, Sunnyvale, Calif.) applied to the top right image to highlight the edge of silicone oil droplets.
Figure 11:
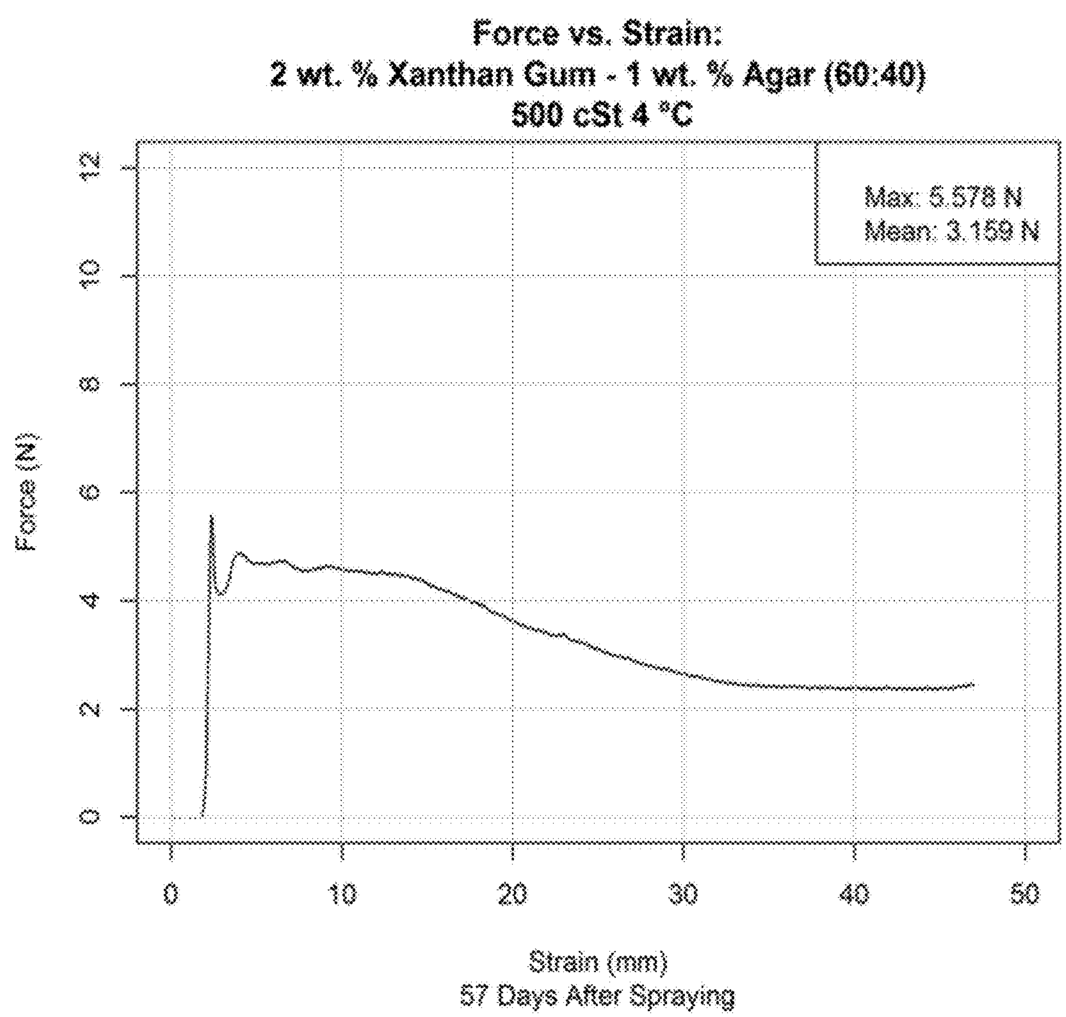
FIG. 11 shows according to an exemplary embodiment of the invention glide force measurements for FIG. 10.
Figure 12:
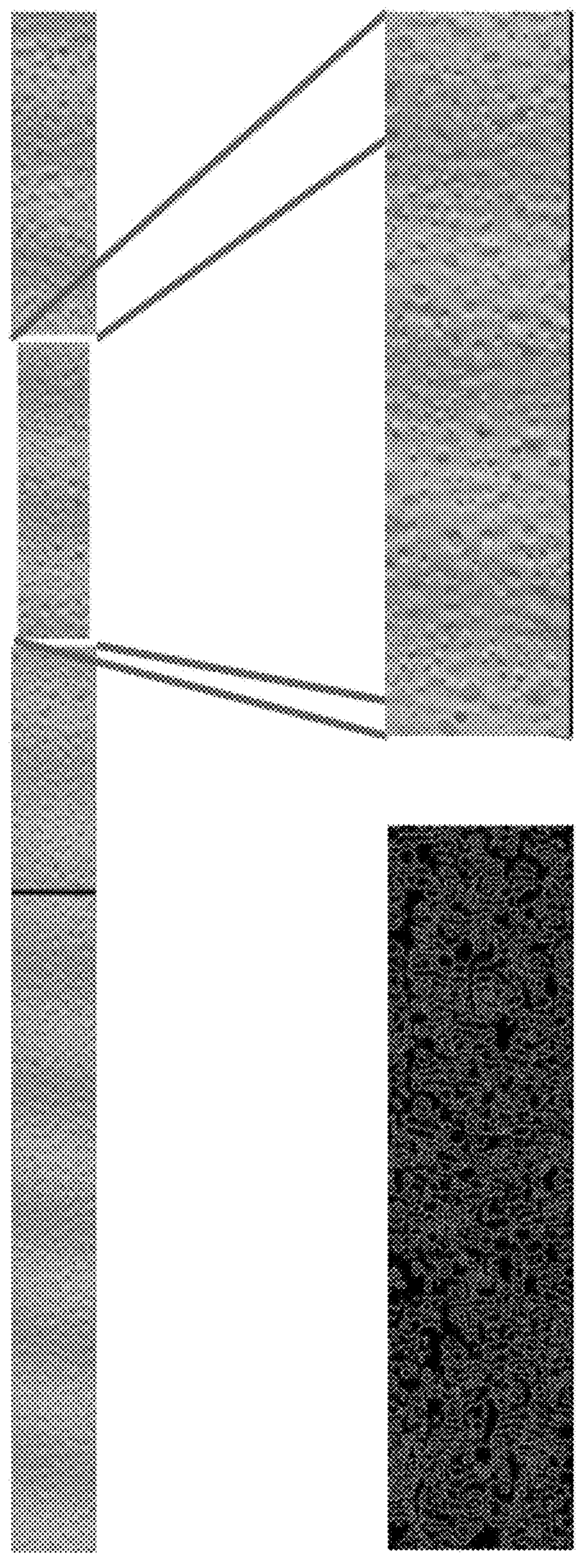
FIG. 12 shows according to an exemplary embodiment of the invention an image of a glass syringe barrel with an emulsion spray of 500 cSt Silicone Oil. The spray is composed of 60% oil/40% water mixture. The water mixture has in it 1% Agar by wt solution. The glass syringe barrel has been filled with an aqueous-based solution and kept for 57 days at 23° C. The top right image in the FIG. 12 is an expanded view of the glass syringe barrel. The bottom right image in FIG. 12 is an image with a Canny Edge detection algorithm (The Mathworks, Sunnyvale, Calif.) applied to the top right image to highlight the edge of silicone oil droplets.
Figure 13:
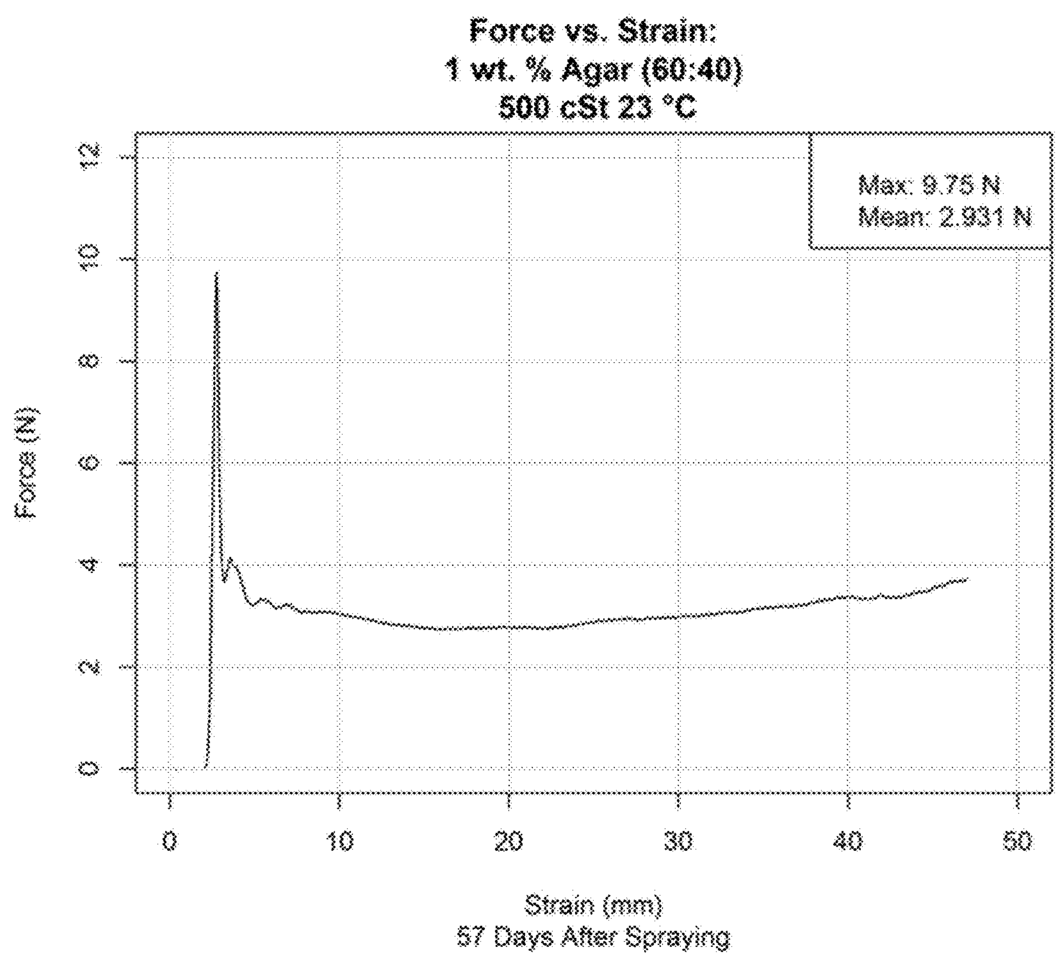
FIG. 13 shows according to an exemplary embodiment of the invention glide force measurements for FIG. 12.
Figure 14:
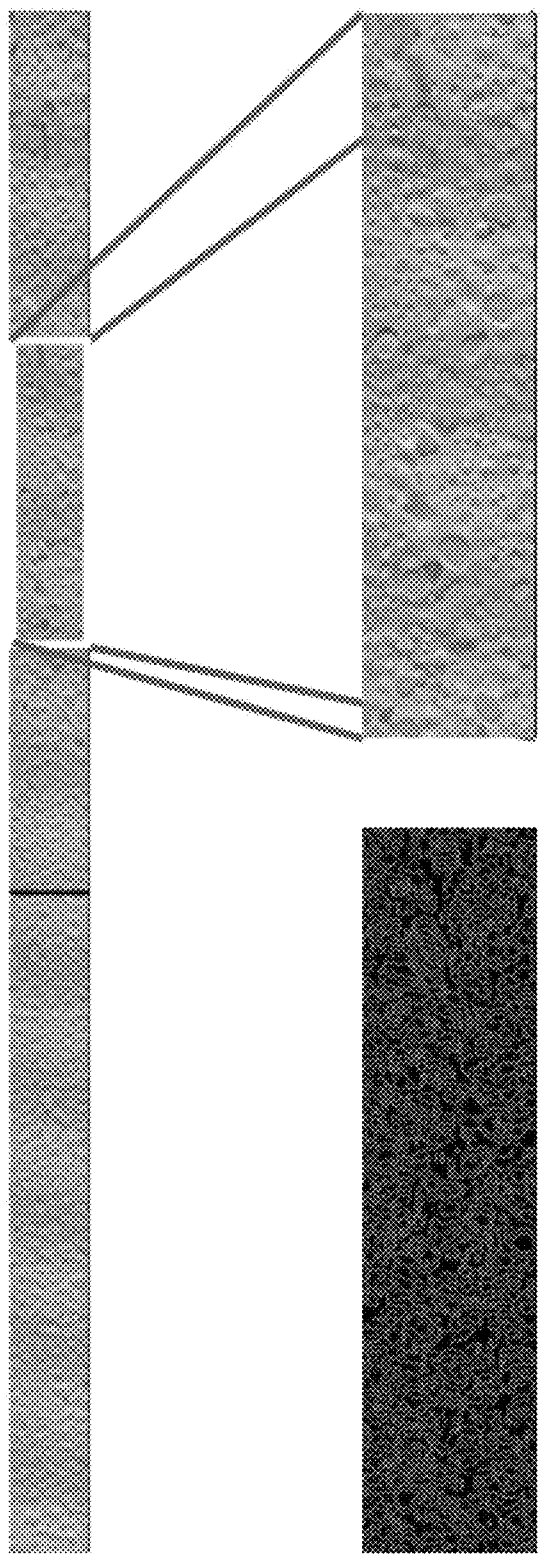
FIG. 14 shows according to an exemplary embodiment of the invention an image of a glass syringe barrel with an emulsion spray of 500 cSt Silicone Oil. The spray is composed of 60% oil/40% water mixture. The water mixture has in it 1% Agar by wt solution. The glass syringe barrel has been filled with an aqueous-based solution and kept for 57 days at 4° C. The top right image in the FIG. 14 is an expanded view of the glass syringe barrel. The bottom right image in FIG. 14 is an image with a Canny Edge detection algorithm (The Mathworks, Sunnyvale, Calif.) applied to the top right image to highlight the edge of silicone oil droplets.
Figure 15:
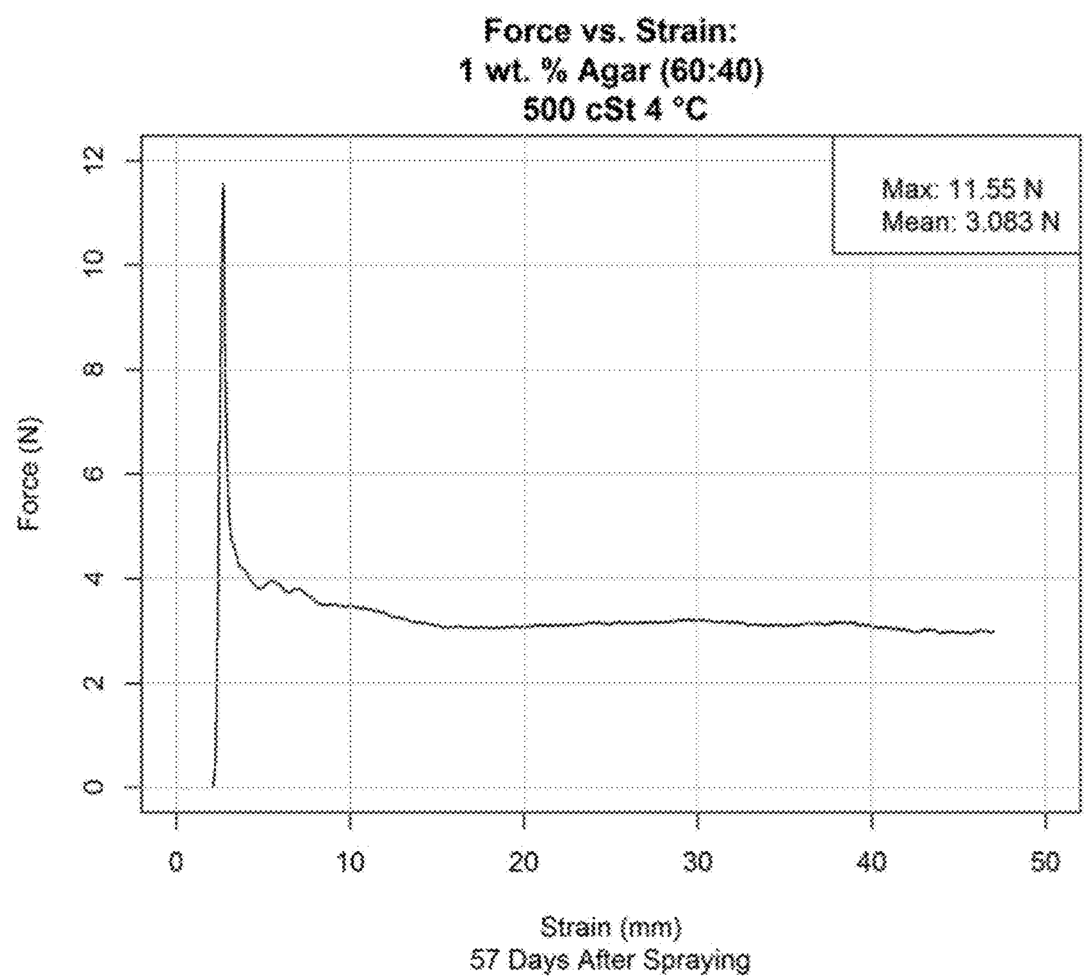
FIG. 15 shows according to an exemplary embodiment of the invention glide force measurements for FIG. 14.
Figure 16:
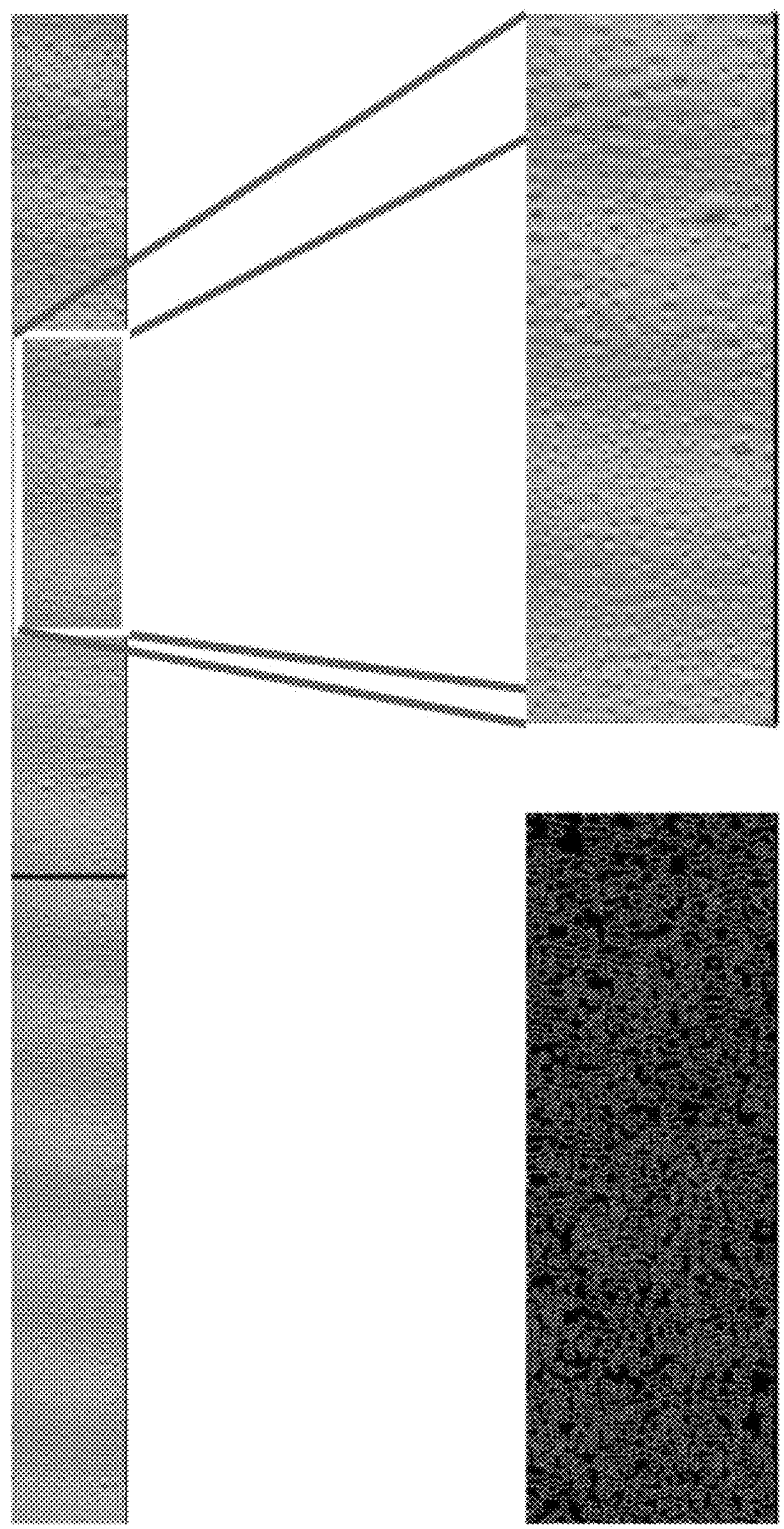
FIG. 16 shows according to an exemplary embodiment of the invention an image of a glass barrel with an emulsion spray of 500 cSt Silicone Oil. The spray is composed of 60% oil/40% water mixture. The water mixture has in it 2% Dextran and 1% Agar by wt solution. The glass syringe barrel has been filled with an aqueous-based solution and kept for 57 days at 23° C. The top right image in the FIG. 16 is an expanded view of the glass syringe barrel. The bottom right image in FIG. 16 is an image with a Canny Edge detection algorithm (The Mathworks, Sunnyvale, Calif.) applied to the top right image to highlight the edge of silicone oil droplets.
Figure 17:
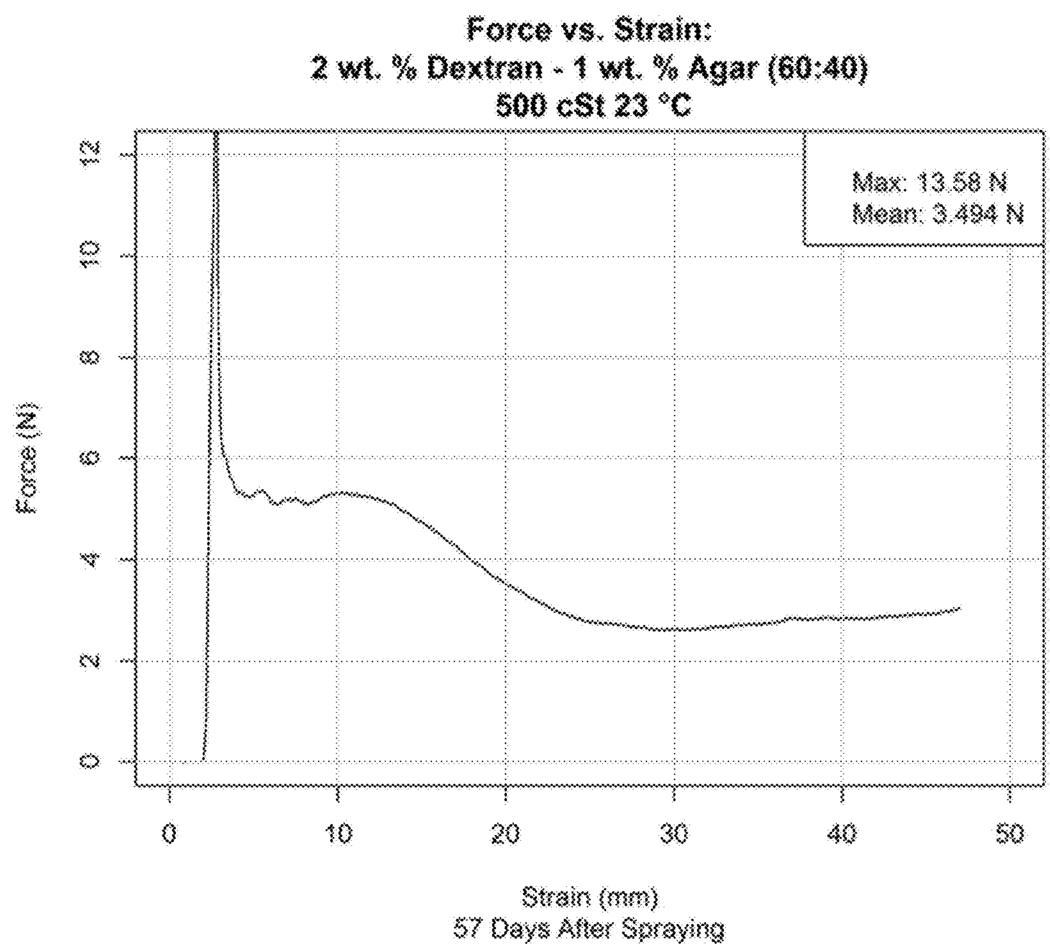
FIG. 17 shows according to an exemplary embodiment of the invention glide force measurements for FIG. 16.
Figure 18:
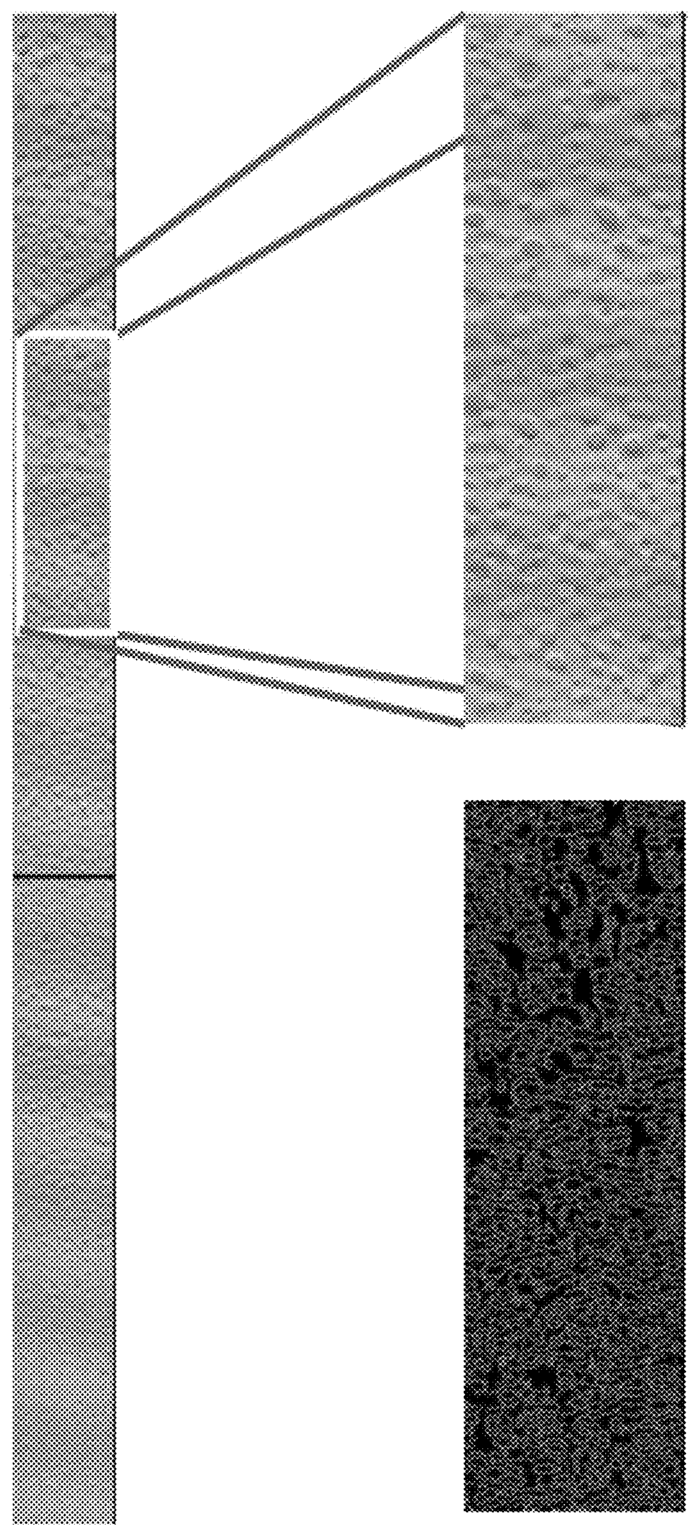
FIG. 18 shows according to an exemplary embodiment of the invention an image of a glass syringe barrel with an emulsion spray of 500 cSt Silicone Oil. The spray is composed of 60% oil/40% water mixture. The water mixture has in it 2% Dextran and 1% Agar by wt solution. The glass syringe barrel has been filled with an aqueous-based solution and kept for 57 days at 4° C. The top right image in the FIG. 18 is an expanded view of the glass syringe barrel. The bottom right image in FIG. 18 is an image with a Canny Edge detection algorithm (The Mathworks, Sunnyvale, Calif.) applied to the top right image to highlight the edge of silicone oil droplets.
Figure 19:
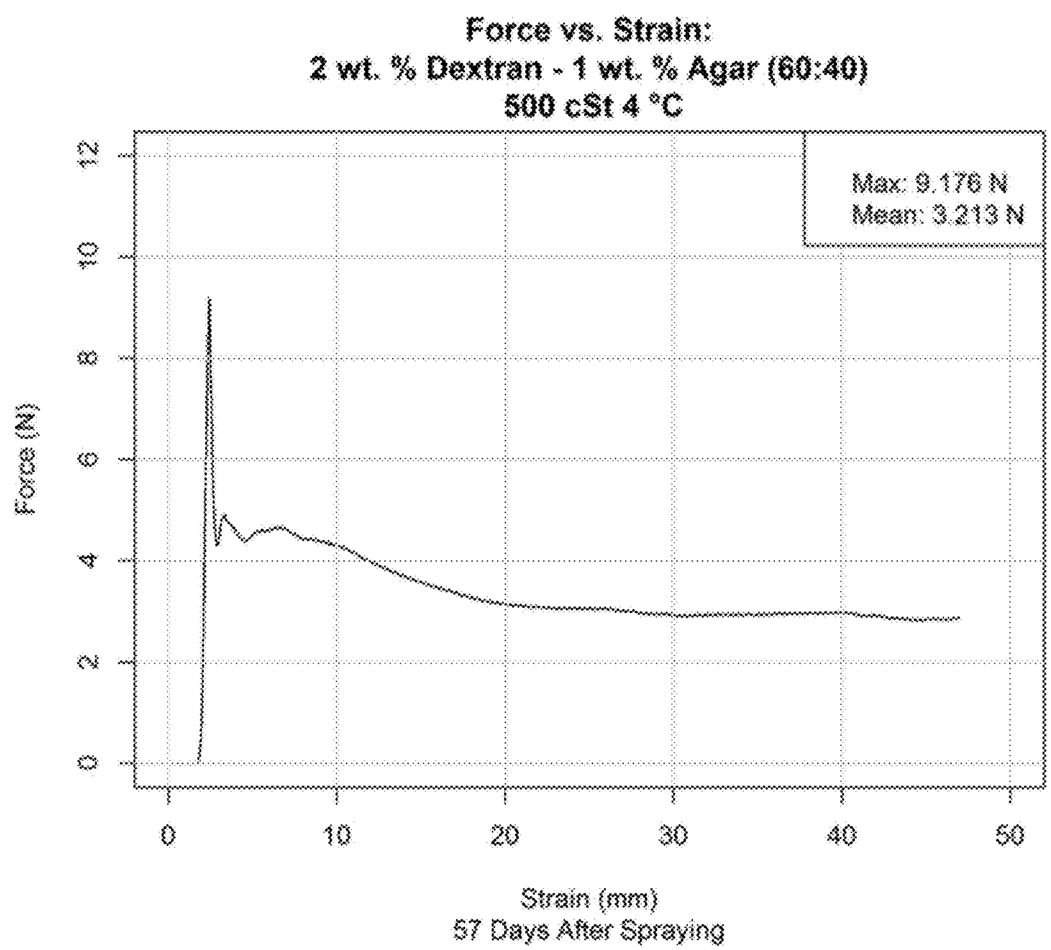
FIG. 19 shows according to an exemplary embodiment of the invention glide force measurements for FIG. 18.
Figure 20:
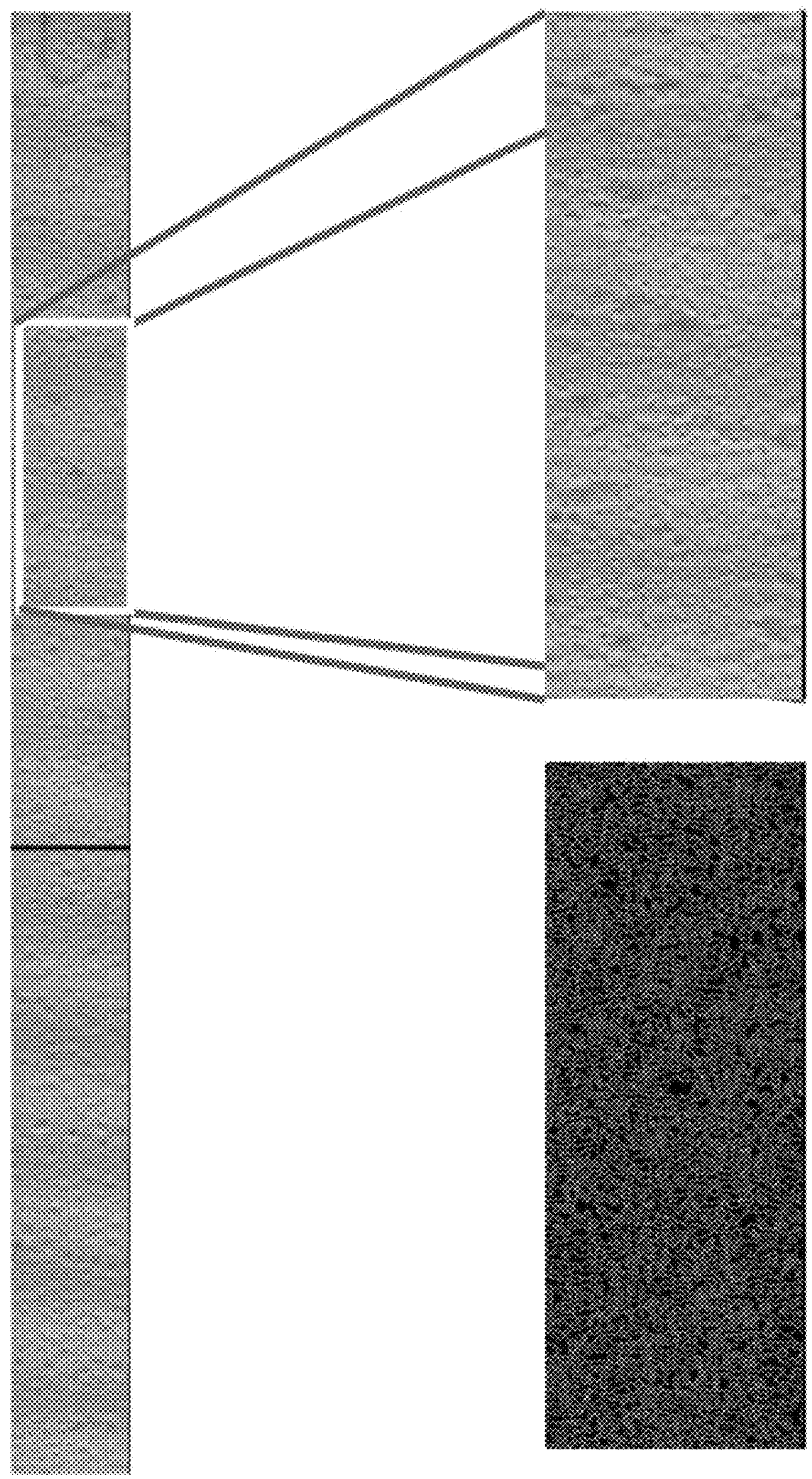
FIG. 20 shows according to an exemplary embodiment of the invention an image of a glass syringe barrel with an emulsion spray of 500 cSt Silicone Oil. The spray is composed of 60% oil/40% water mixture. The water mixture has in it 2% CMC and 1% Agar by wt solution. The glass syringe barrel has been filled with an aqueous-based solution and kept for 57 days at 23° C. The top right image in the FIG. 20 is an expanded view of the glass syringe barrel. The bottom right image in FIG. 20 is an image with a Canny Edge detection algorithm (The Mathworks, Sunnyvale, Calif.) applied to the top right image to highlight the edge of silicone oil droplets.
Figure 21:
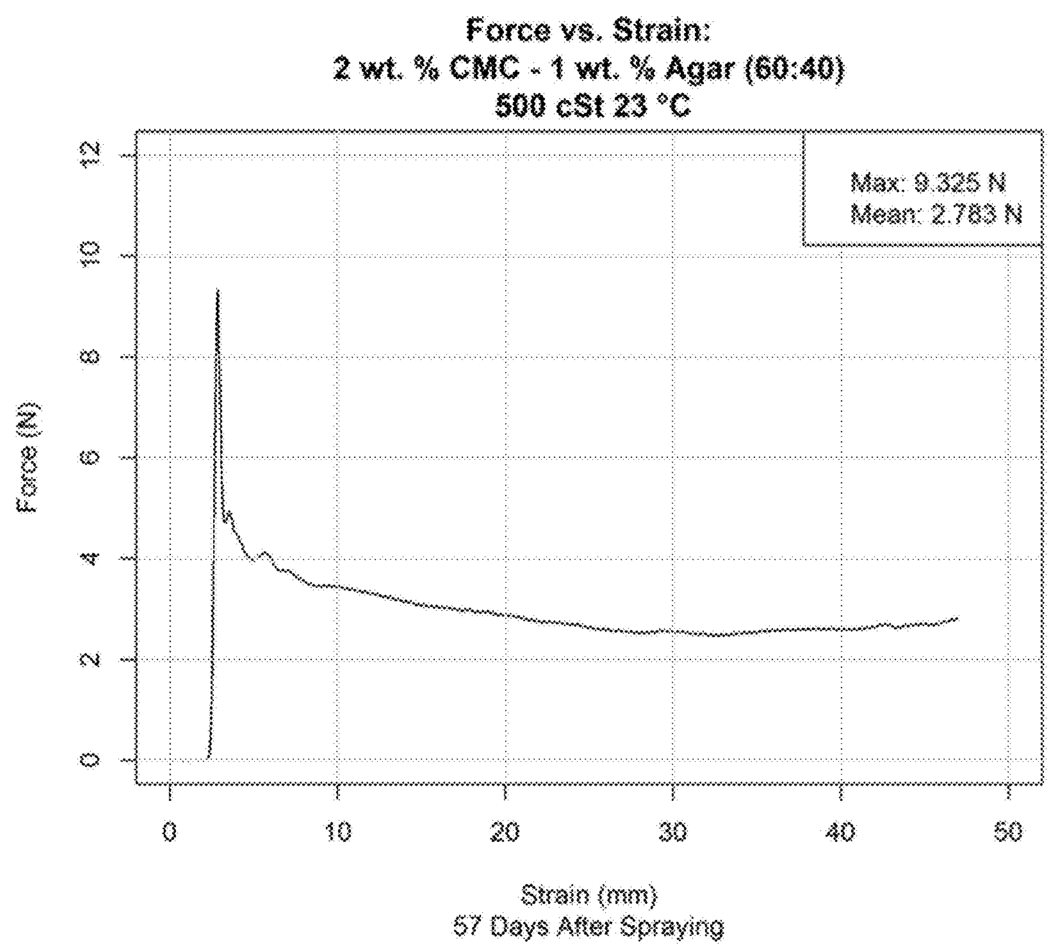
FIG. 21 shows according to an exemplary embodiment of the invention glide force measurements for FIG. 20.
Figure 22:
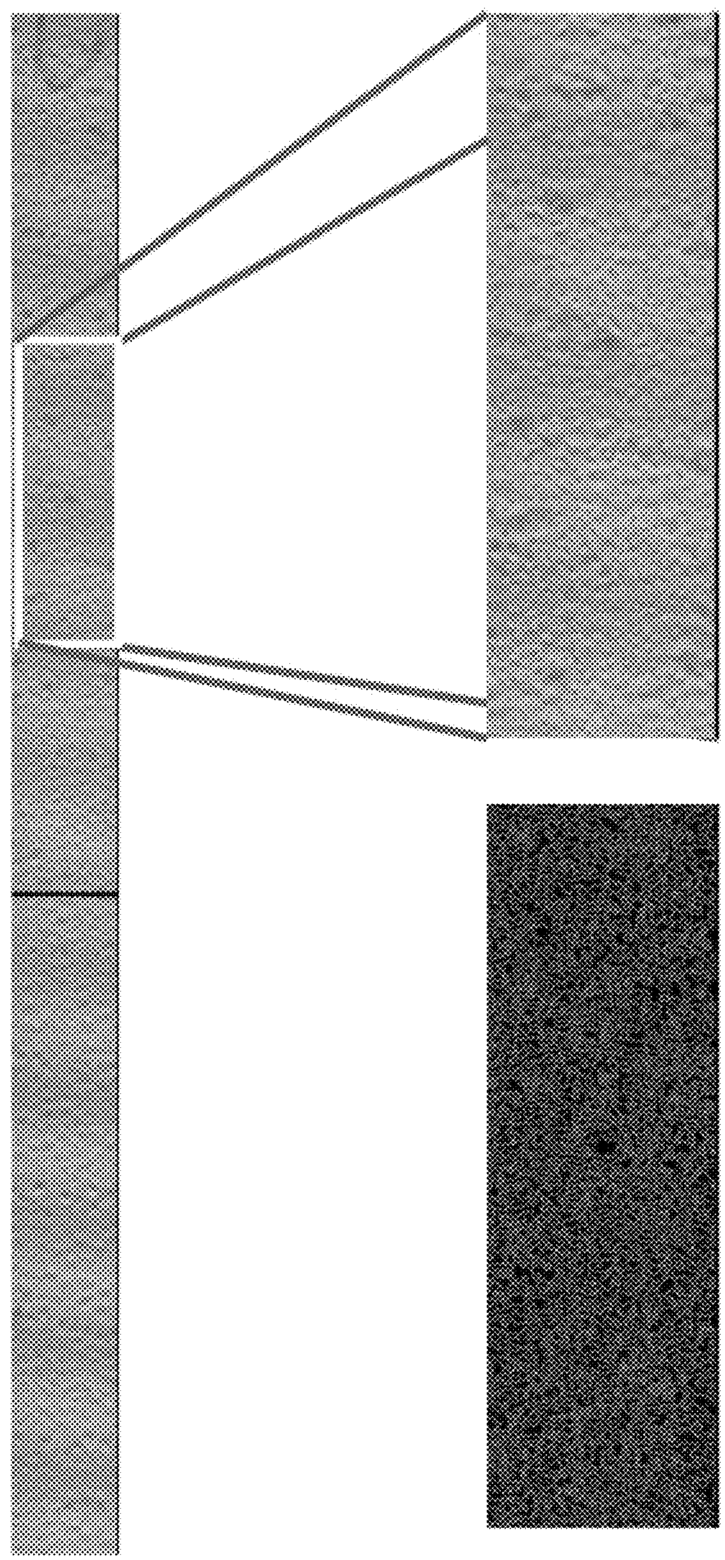
FIG. 22 shows according to an exemplary embodiment of the invention an image of a glass syringe barrel with an emulsion spray of 1000 cSt Silicone Oil. The spray is composed of 60% oil/40% water mixture. The water mixture has in it 1% Agar by wt solution. The glass syringe barrel has been filled with an aqueous-based solution and kept for 57 days at 23° C. The top right image in the FIG. 22 is an expanded view of the glass syringe barrel. The bottom right image in FIG. 22 is an image with a Canny Edge detection algorithm (The Mathworks, Sunnyvale, Calif.) applied to the top right image to highlight the edge of silicone oil droplets.
Figure 23:
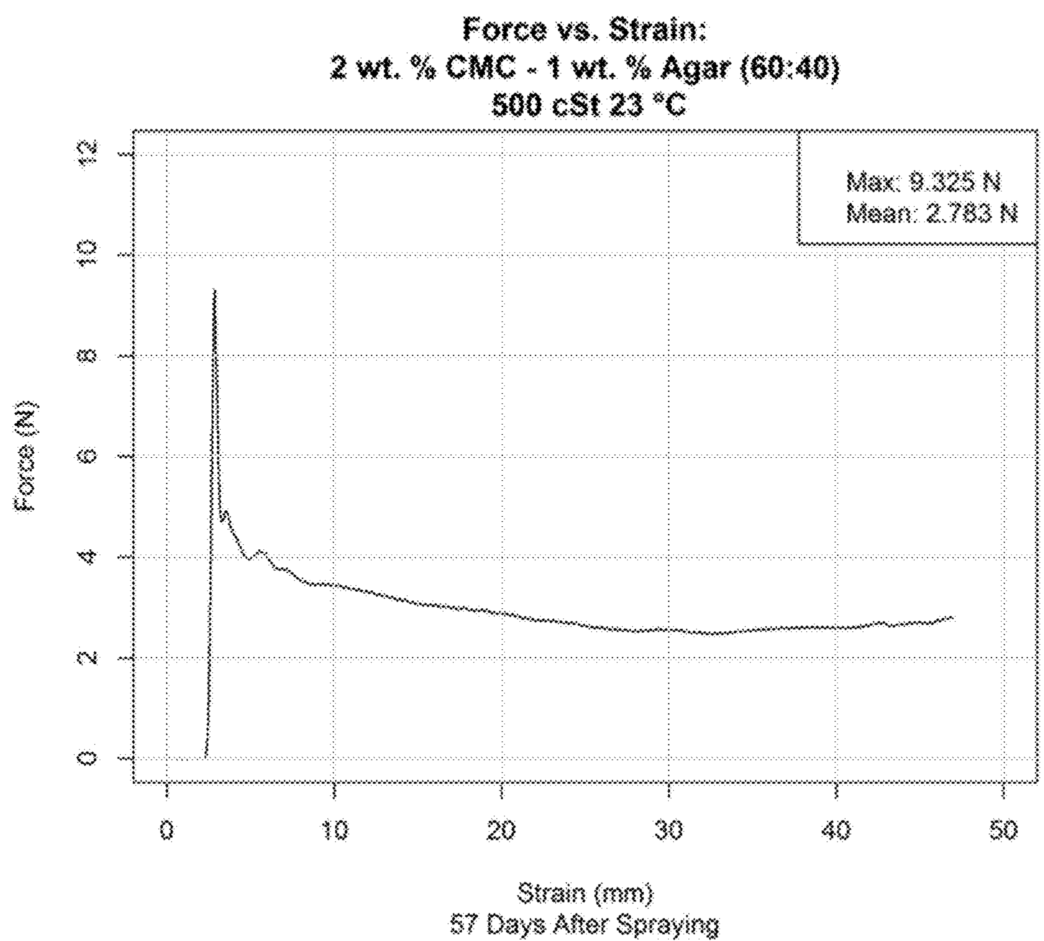
FIG. 23 shows according to an exemplary embodiment of the invention glide force measurements for FIG. 22.
Figure 24:
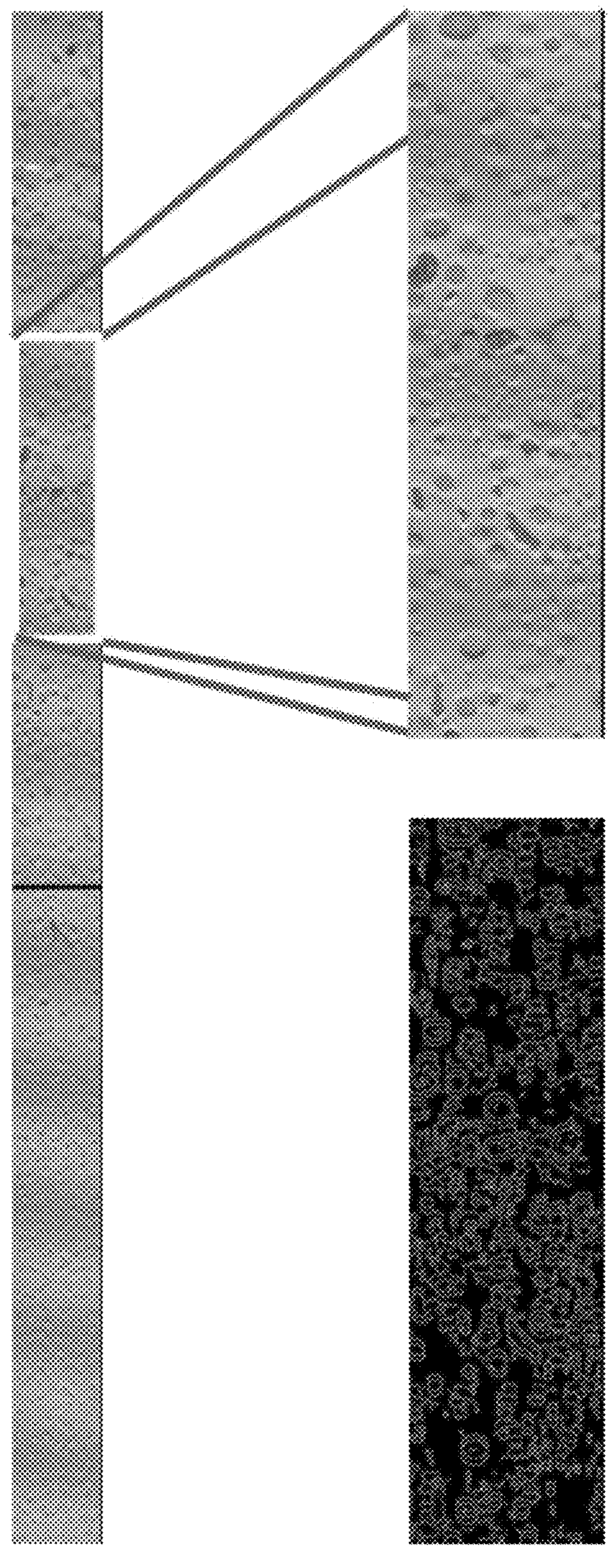
FIG. 24 shows according to an exemplary embodiment of the invention an image of a glass syringe barrel with an emulsion spray of 1000 cSt Silicone Oil. The spray is composed of 60% oil/40% water mixture. The water mixture has in it 1% Agar by wt solution. The glass syringe barrel has been filled with an aqueous-based solution and kept for 57 days at 4° C. The top right image in the FIG. 24 is an expanded view of the glass syringe barrel. The bottom right image in FIG. 24 is an image with a Canny Edge detection algorithm (The Mathworks, Sunnyvale, Calif.) applied to the top right image to highlight the edge of silicone oil droplets.
Figure 25:
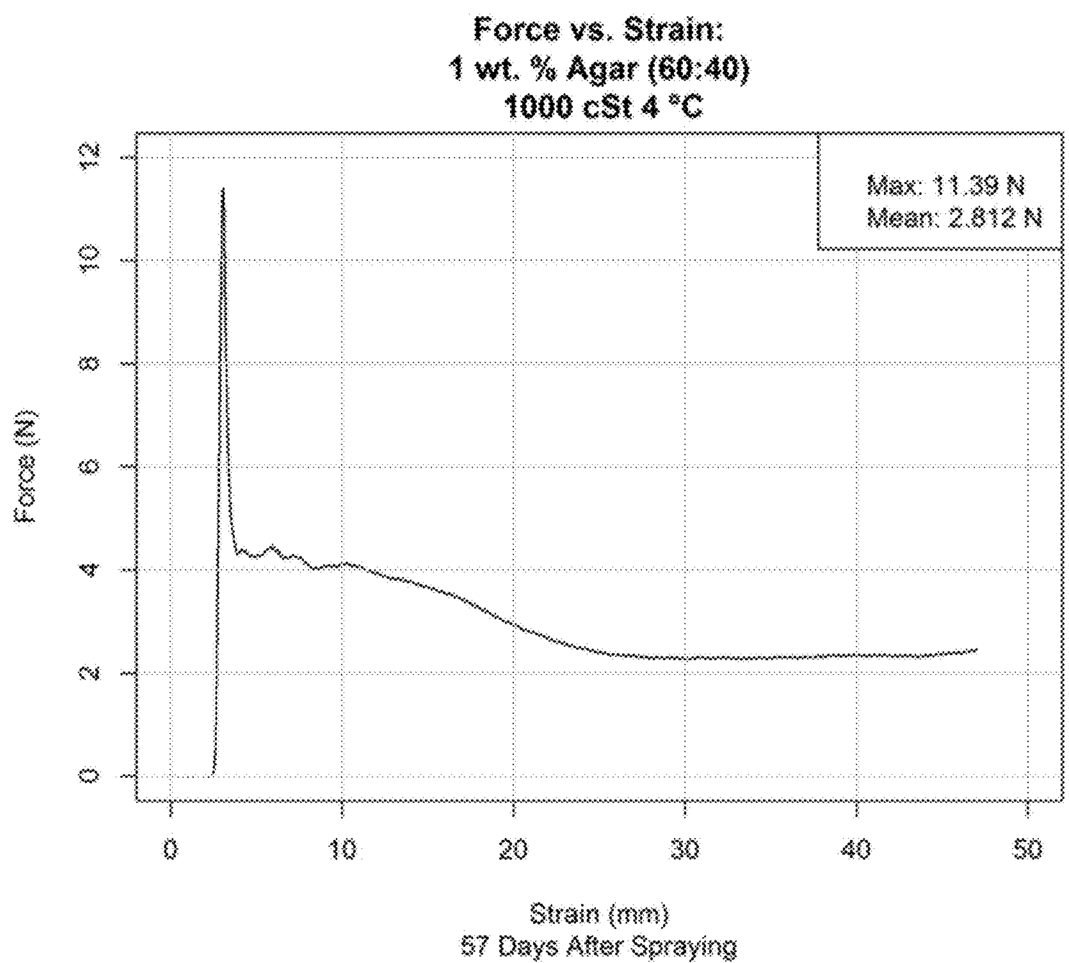
FIG. 25 shows according to an exemplary embodiment of the invention glide force measurements for FIG. 24.
Figure 26:
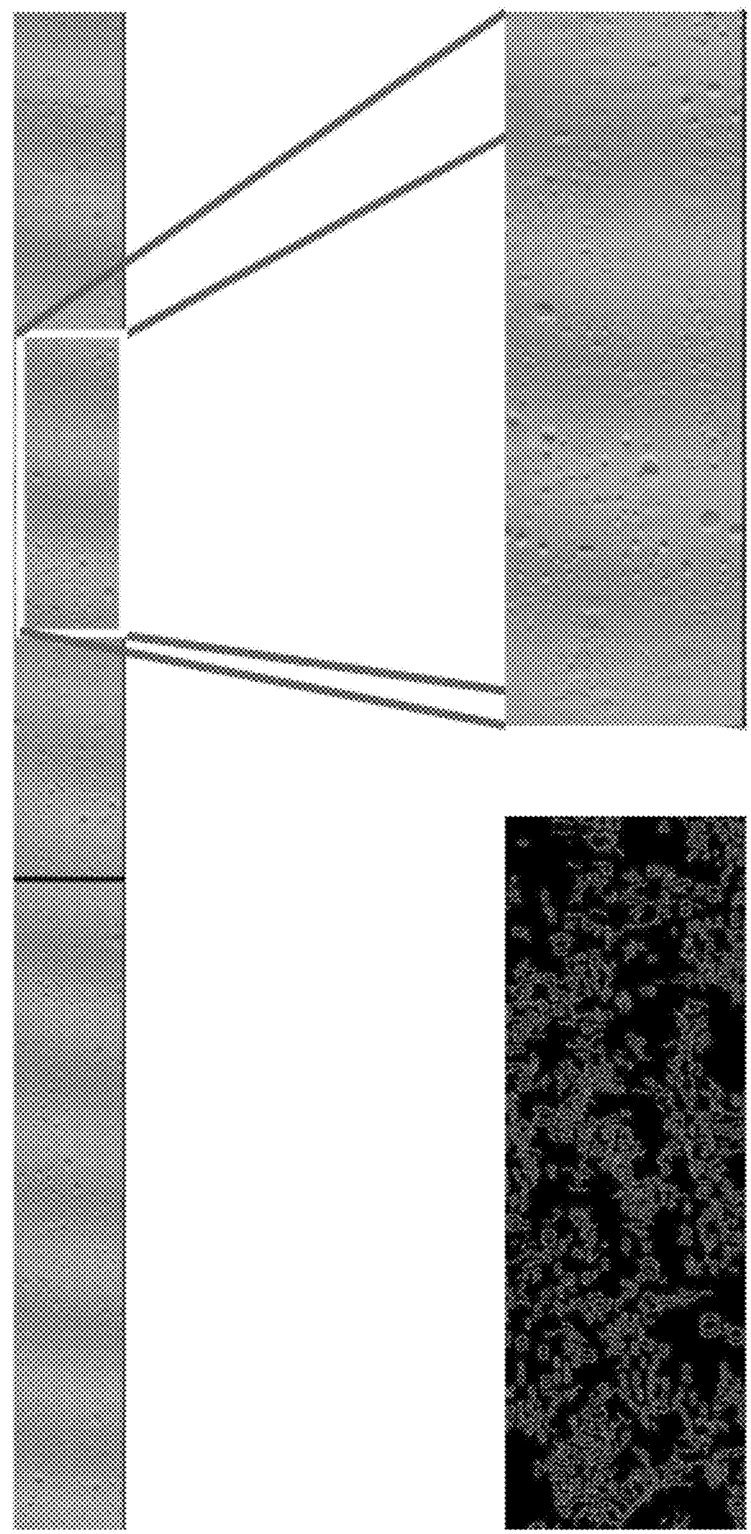
FIG. 26 shows according to an exemplary embodiment of the invention an image of a glass syringe barrel with an emulsion spray of 1000 cSt Silicone Oil. The spray is composed of 60% oil/40% water mixture. The water mixture has in it 2% Xanthan Gum and 1% Agar by wt solution. The glass syringe barrel has been filled with an aqueous-based solution and kept for 57 days at 4° C. The top right image in the FIG. 26 is an expanded view of the glass syringe barrel. The bottom right image in FIG. 26 is an image with a Canny Edge detection algorithm (The Mathworks, Sunnyvale, Calif.) applied to the top right image to highlight the edge of silicone oil droplets.
Figure 27:
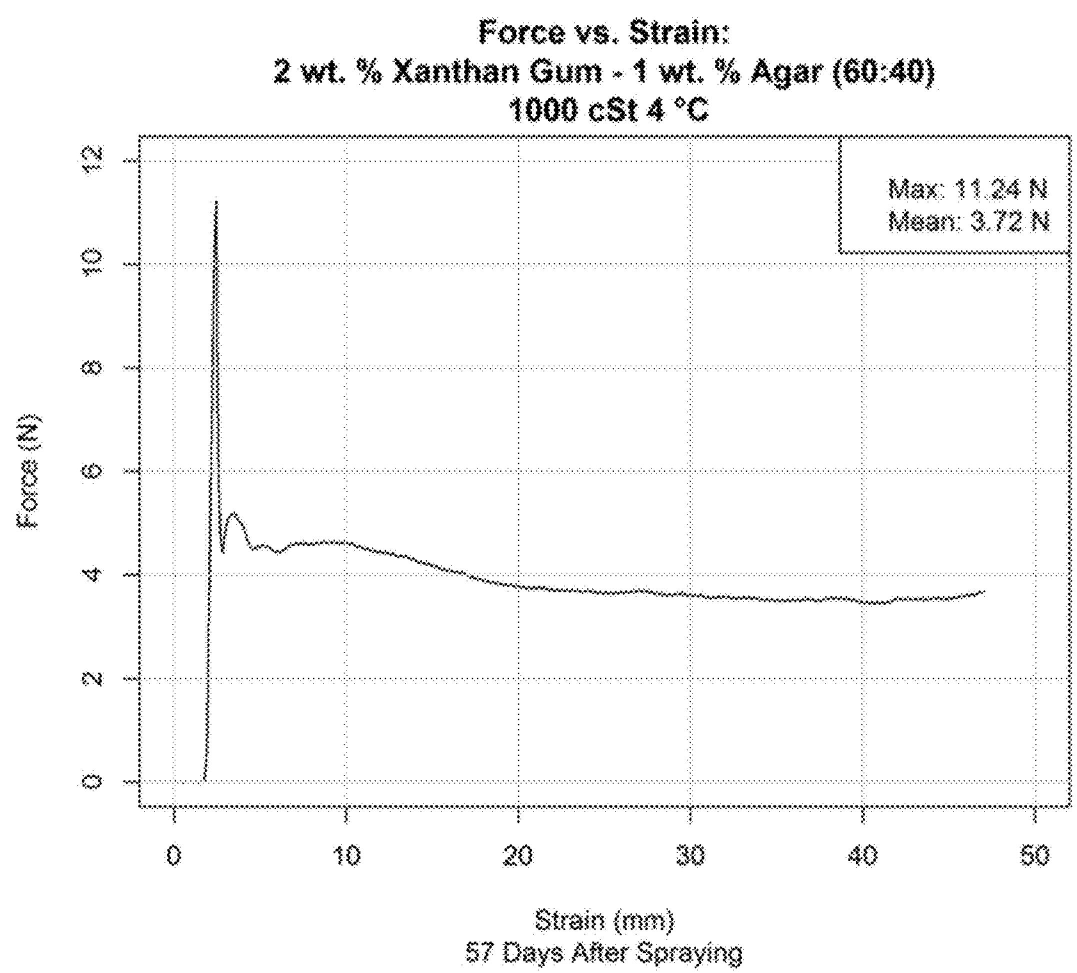
FIG. 27 shows according to an exemplary embodiment of the invention glide force measurements for FIG. 26.
Figure 28:
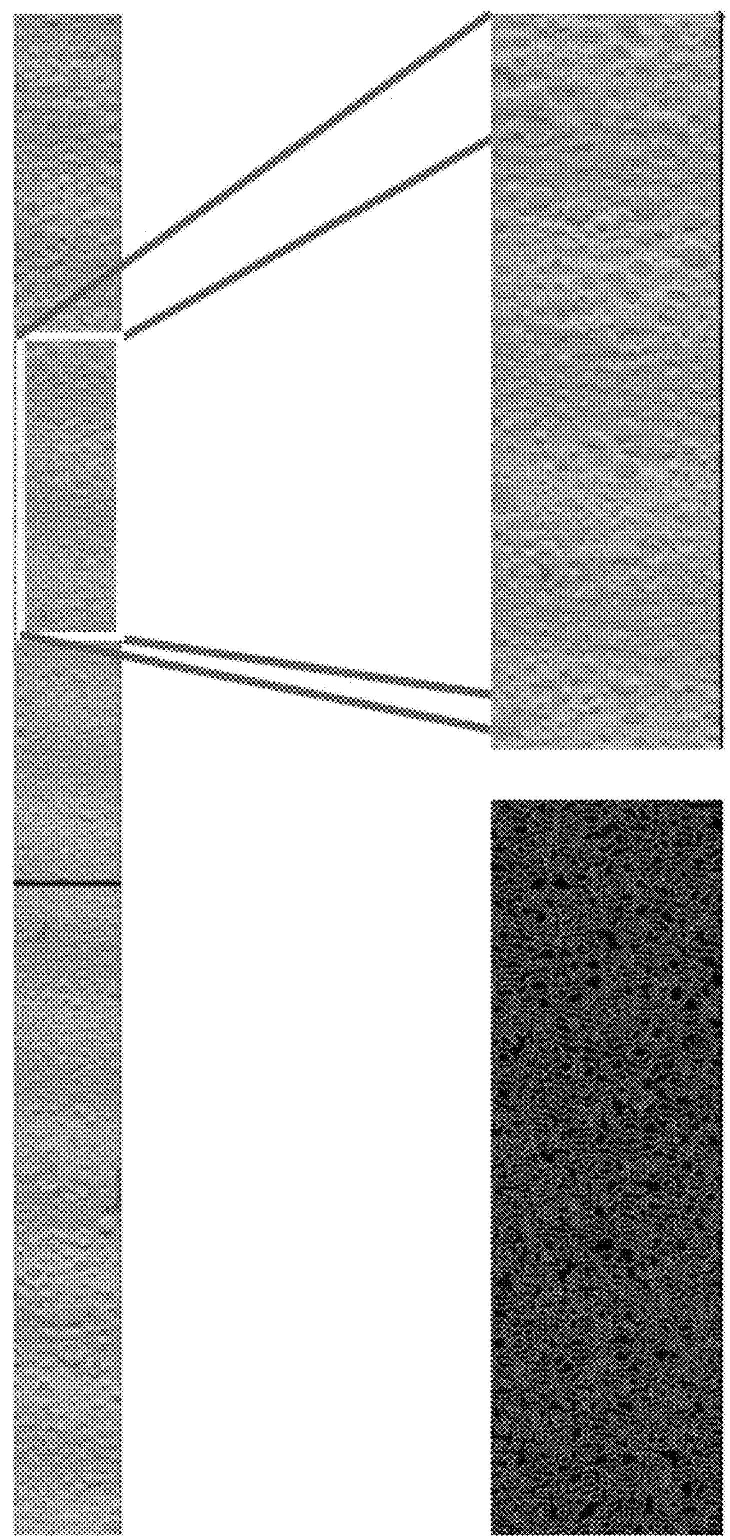
FIG. 28 shows according to an exemplary embodiment of the invention an image of a glass syringe barrel with an emulsion spray of 1000 cSt Silicone Oil. The spray is composed of 60% oil/40% water mixture. The water mixture has in it 2% Dextran and 1% Agar by wt solution. The glass syringe barrel has been filled with an aqueous-based solution and kept for 57 days at 4° C. The top right image in the FIG. 28 is an expanded view of the glass syringe barrel. The bottom right image in FIG. 28 is an image with a Canny Edge detection algorithm (The Mathworks, Sunnyvale, Calif.) applied to the top right image to highlight the edge of silicone oil droplets.
Figure 29:
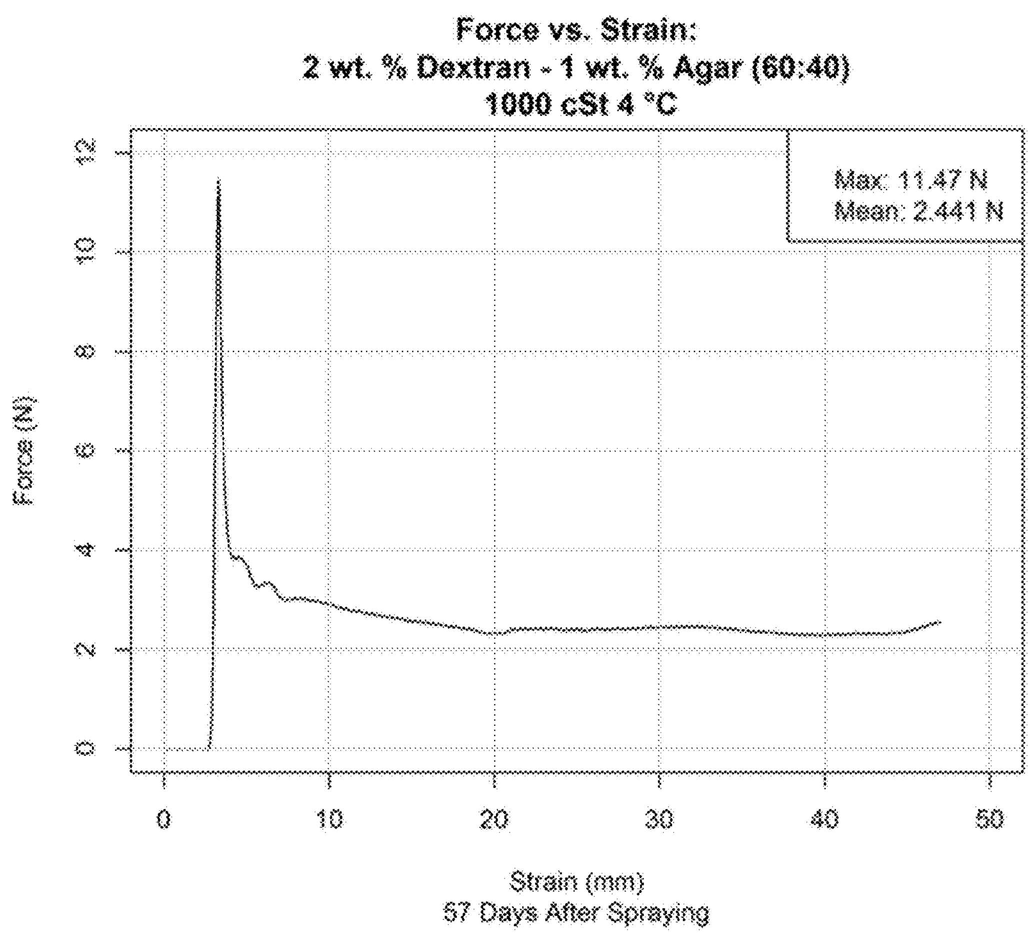
FIG. 29 shows according to an exemplary embodiment of the invention glide force measurements for FIG. 28.

Weight composition for FIGS. 6-29 are in a Table shown in FIG. 30. Water continuous emulsions were prepared by dispersing oil in an Agar solution using a high energy mixing unit (AE500S-P 500 shear emulsifying machine, Huanyu Instrument, Zhejiang, (China) followed by the addition of Xanthan Gum solution under continuous shearing for 5 minutes at 11,000 rpm. It is noted that Agar comes in powder form and has to be dissolved in water above 85 degrees Celsius.

Emulsion Application

A typical emulsion volume sprayed is 0.5-10 μL with a flow rate of 2.5 slm (standard liter per minute) and nozzle temperature of 65 degrees Celsius. The spray system started dispensing the emulsion at 30 mm outside of the syringe barrel and stopped at 40 mm inside the syringe barrel. The duration of the spray process is 1 second.

Measurement of Glide Force

The determination of the break-loose force and glide force for the syringes was carried out using a Zwick Roell (Kennesaw, Ga.) test device based on standards EN ISO 7886-1, EN ISO 11499 and ISO 11040-4.

The force applied to a syringe plunger during the injection of a drug formulation via a needle is dissipated in three ways: (a) overcoming the resistance force of the syringe plunger; (b) imparting kinetic energy to the liquid; and (c) forcing the liquid through the needle.

In the force vs. displacement plots shown in the figures three different portions can be identified: A first portion related to the force required to displace the plunger, namely the plunger-stopper breakloose force (PBF). This maximum value is followed by a plateau (second portion) indicating that the streamline of the formulation through the needle occurs with roughly a constant force. In this portion the average load required to sustain the movement of the plunger to expel the content of the syringe is called the dynamic glide force (DGF). During the third portion, the force rapidly increases because of the compression of syringe plunger against the end of syringe body (not depicted in the figures).

After the spray process, the syringe barrels may be inspected using the lubricant coverage quality control method and system and method as described in U.S. Pat. No. 9,327,079 assigned to ZebraSci, Inc.

What is claimed is:

1. A medical drug delivery device, comprising: a syringe barrel with an interior surface lubricated with an emulsion of a hydrophobic liquid oil in a matrix of water-soluble polysaccharides, wherein one type of the polysaccharides is Agar.

2. The device as set forth in claim 1, wherein the emulsion comprises 1-10 percent Agar.

3. The device as set forth in claim 1, wherein the polysaccharides further comprise Xantham Gum, Dextrum, Cellulose, or a combination thereof.

4. The device as set forth in claim 1, wherein the emulsion has a friction of less than 4N.

5. The device as set forth in claim 1, wherein the emulsion is temperature stable in a range of 4-23 degrees Celsius.

6. The device as set forth in claim 1, wherein the emulsion is stable for a period of at least 60 days.

7. The device as set forth in claim 1, wherein the hydrophobic liquid oil has a viscocity in the range 20-12,500 cSt.

8. A method of lubricating a medical drug delivery device, comprising spraying an emulsion onto the interior surface of a syringe barrel, wherein the emulsion comprises of a hydrophobic liquid oil on a matrix of water-soluble polysaccharides, wherein one type of the polysaccharides is Agar.

9. The method as set forth in claim 8, wherein the emulsion is sprayed on with a volume of 0.5-10 microliter and with a flow rate of 1-5 standard liter per minute.

10. The method as set forth in claim 8, wherein the spaying starts at about 30 mm outside the syringe barrel and stops at about 40 mm inside the syringe barrel for a duration of about 1 second.

11. The method as set forth in claim 8, wherein the emulsion comprises 1-10 percent agar.

12. The method as set forth in claim 8, wherein the polysaccharides further comprise Xantham Gum, Dextrum, Cellulose, or a combination thereof.

13. The method as set forth in claim 8, wherein the emulsion has a friction of less than 4N.

14. The method as set forth in claim 8, wherein the emulsion is temperature stable in a range of 4-23 degrees Celsius.

15. The method as set forth in claim 8, wherein the emulsion is stable for a period of at least 60 days.

16. The method as set forth in claim 8, wherein the hydrophobic liquid oil has a viscocity in the range 20-12,500 cSt.

* * * * *